(12) United States Patent
Levendowski et al.

(10) Patent No.: US 8,684,006 B2
(45) Date of Patent: Apr. 1, 2014

(54) SYSTEMS AND METHODS FOR OPTIMIZING ORAL APPLIANCE THERAPY FOR THE TREATMENT OF SLEEP APNEA

(75) Inventors: Daniel Levendowski, Carlsbad, CA (US); Todd Morgan, Encinitas, CA (US); Victoria Melzer, Encinitas, CA (US)

(73) Assignee: Advanced Brain Monitoring, Inc., Carlsbad, CA (US)

( * ) Notice: Subject to any disclaimer, the term of this patent is extended or adjusted under 35 U.S.C. 154(b) by 0 days.

(21) Appl. No.: 13/071,354

(22) Filed: Mar. 24, 2011

(65) Prior Publication Data

US 2011/0232652 A1  Sep. 29, 2011

Related U.S. Application Data

(60) Provisional application No. 61/318,111, filed on Mar. 26, 2010.

(51) Int. Cl.
*A61F 5/56* (2006.01)
*A61C 5/14* (2006.01)

(52) U.S. Cl.
USPC ............................ 128/848; 128/859; 128/861

(58) Field of Classification Search
USPC .................. 128/848, 859, 860–861; 602/902
See application file for complete search history.

(56) References Cited

U.S. PATENT DOCUMENTS

| | | | |
|---|---|---|---|
| 3,473,225 A | 10/1969 | Deuschle et al. | |
| 3,838,513 A | 10/1974 | Katz et al. | |
| 3,878,610 A | 4/1975 | Coscina | |
| 4,146,963 A | 4/1979 | Schreinemakers | |
| 4,227,877 A | 10/1980 | Tureaud et al. | |
| 4,569,342 A | 2/1986 | von Nostitz | |
| 5,076,785 A | 12/1991 | Tsai | |
| 5,313,960 A | 5/1994 | Tomasi | |
| 5,336,086 A | 8/1994 | Simmen et al. | |
| 5,365,945 A | 11/1994 | Halstrom | |

(Continued)

OTHER PUBLICATIONS

Pancherz, Hans, "Treatment of Class II malocclusions by jumping the bite with the Herbst appliance, A cephalometric investigation," The Department of Orthodontics, School of Dentistry, University of Lund, 1979, the C.V. Mosby Co., 20 pages.

(Continued)

*Primary Examiner* — Patricia Bianco
*Assistant Examiner* — Camtu Nguyen
(74) *Attorney, Agent, or Firm* — Procopio, Cory, Hargreaves & Savitch, LLP

(57) ABSTRACT

Systems and methods are provided for optimizing the treatment of obstructive sleep apnea (OSA) using an oral appliance. The oral appliance can be configured by non-dental staff to safely conform to the dentition of a patient. The appliance includes configurable trays that include retention material that conforms to the dentition of the patient. The position of the upper and lower trays relative to one another can be adjusted both horizontally and vertically. The position of the upper and lower trays can be locked into place to maintain the position of the trays at a preferred treatment position. Methods for creating an appliance customized for a patient are also provided. Methods for using the customized appliance in combination with sleep study data is also provide. Methods for using the customized appliance to with pre-operative assessments and sleep study data to predict and reduce the risk of perioperative complications are also provided.

24 Claims, 22 Drawing Sheets

(56) References Cited

U.S. PATENT DOCUMENTS

| | | | |
|---|---|---|---|
| 5,409,017 A | 4/1995 | Lowe | |
| 5,427,117 A | 6/1995 | Thornton | |
| 5,499,633 A | 3/1996 | Fenton | |
| 5,536,168 A * | 7/1996 | Bourke | 433/6 |
| 5,537,994 A | 7/1996 | Thornton | |
| 5,570,704 A | 11/1996 | Buzzard et al. | |
| 5,611,355 A | 3/1997 | Hilsen | |
| 5,755,219 A | 5/1998 | Thornton | |
| 5,807,100 A | 9/1998 | Thornton | |
| 5,810,013 A | 9/1998 | Belfer | |
| 5,829,441 A | 11/1998 | Kidd et al. | |
| 5,954,048 A | 9/1999 | Thornton | |
| 5,983,892 A | 11/1999 | Thornton | |
| 6,109,265 A | 8/2000 | Frantz et al. | |
| 6,170,485 B1 * | 1/2001 | Orrico | 128/848 |
| 6,305,376 B1 | 10/2001 | Thornton | |
| 6,374,824 B1 | 4/2002 | Thornton | |
| 6,408,851 B1 | 6/2002 | Karell | |
| 6,857,428 B2 | 2/2005 | Thornton | |
| 7,174,895 B2 | 2/2007 | Thornton | |
| 7,243,650 B2 | 7/2007 | Thornton | |
| 7,520,281 B1 * | 4/2009 | Nahabedian | 128/848 |
| 7,597,103 B2 | 10/2009 | Thornton | |
| 7,677,889 B2 | 3/2010 | Thornton | |
| 7,748,386 B2 | 7/2010 | Thornton | |
| 7,909,035 B2 | 3/2011 | Thornton | |
| 7,992,558 B2 | 8/2011 | Thornton | |
| 8,020,276 B2 | 9/2011 | Thornton | |
| 8,236,216 B2 | 8/2012 | Thornton | |
| 2002/0189620 A1 | 12/2002 | L'Estrange et al. | |
| 2005/0175954 A1 * | 8/2005 | Zacher | 433/5 |
| 2005/0236003 A1 | 10/2005 | Meader | |
| 2008/0006273 A1 | 1/2008 | Thornton | |
| 2008/0006274 A1 | 1/2008 | Thornton | |
| 2008/0135056 A1 * | 6/2008 | Nelissen | 128/848 |
| 2010/0218773 A1 | 9/2010 | Thornton | |
| 2010/0263677 A1 | 10/2010 | Thornton | |
| 2010/0316973 A1 * | 12/2010 | Remmers et al. | 433/214 |

OTHER PUBLICATIONS

Remmer, K. Ross et al., "Cephalometric changes associated with treatment using the activator, the Fränkel applicance, and the fixed appliance," American Journal of Orthodontics, vol. 88 No. 5, Nov. 1985, The C.V. Mosby Company, 10 pages.

International Search Report and Written Opinion issued in PCT/US2011/030075 on Nov. 30, 2011, 8 pages.

Pancherz, at al. "Treatment of Class II malocclusions by jumping the bite with the Herbst appliance: A cephalometric investigation," American Journal of Orthodontics, vol. 76, No. 4, Oct. 1979, pp. 423-442.

Remmer, et al. "Cephalometric changes associated with treatment using the activator, the Frankel appliance, and the fixed appliance," American Journal of Orthodontics, vol. 88, No. 5, Nov. 1985, pp. 363-372.

Kuna, et al. "Effect of Progressive Mandibular Advancement on Pharyngeal Airway Size in Anesthetized Adults," NIH Public Access Author Manuscript, Anesthesiology, 109(4): 605-612, Oct. 2008, 16 pages.

Pancherz, "Treatment of Class II malocclusions by jumping the bite with the Herbst appliance: A cephalometric investigation," American Journal of Orthodontics, vol. 76, Issue 4, Oct. 1979, pp. 423-442.

Remmer, et al. "Cephalometric changes associated with treatment using the activator, the Fränkel appliance, and the fixed appliance," American Journal of Orthodontics, vol. 88, Issue 5, Nov. 1985, pp. 363-372.

* cited by examiner

Look-up Table to Determine 70% Maximum Advancement

| Max Setting | Neutral position setting | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| 5 | 4 | | | | | | | | | | | |
| 6 | 4 | 5 | | | | | | | | | | |
| 7 | 5 | 5 | 6 | | | | | | | | | |
| 8 | 6 | 6 | 6 | 7 | | | | | | | | |
| 9 | 6 | 7 | 7 | 7 | 8 | | | | | | | |
| 10 | 7 | 7 | 8 | 8 | 8 | 9 | | | | | | |
| 11 | 8 | 8 | 8 | 9 | 9 | 9 | 10 | | | | | |
| 12 | 9 | 9 | 9 | 9 | 10 | 10 | 10 | 11 | | | | |
| 13 | 9 | 10 | 10 | 10 | 10 | 11 | 11 | 11 | 12 | | | |
| 14 | 10 | 10 | 11 | 11 | 11 | 11 | 12 | 12 | 12 | 13 | | |
| 15 | 11 | 11 | 11 | 12 | 12 | 12 | 12 | 13 | 13 | 13 | 14 | |
| 16 | 11 | 12 | 12 | 12 | 13 | 13 | 13 | 13 | 14 | 14 | 14 | 15 |
| 17 | 12 | 12 | 13 | 13 | 13 | 14 | 14 | 14 | 14 | 15 | 15 | 15 |
| 18 | 13 | 13 | 13 | 14 | 14 | 14 | 15 | 15 | 15 | 15 | 16 | 16 |
| 19 | 13 | 14 | 14 | 14 | 15 | 15 | 15 | 16 | 16 | 16 | 16 | 17 |
| 20 | | 14 | 15 | 15 | 15 | 16 | 16 | 17 | 17 | 17 | 17 | 17 |

FIG. 11

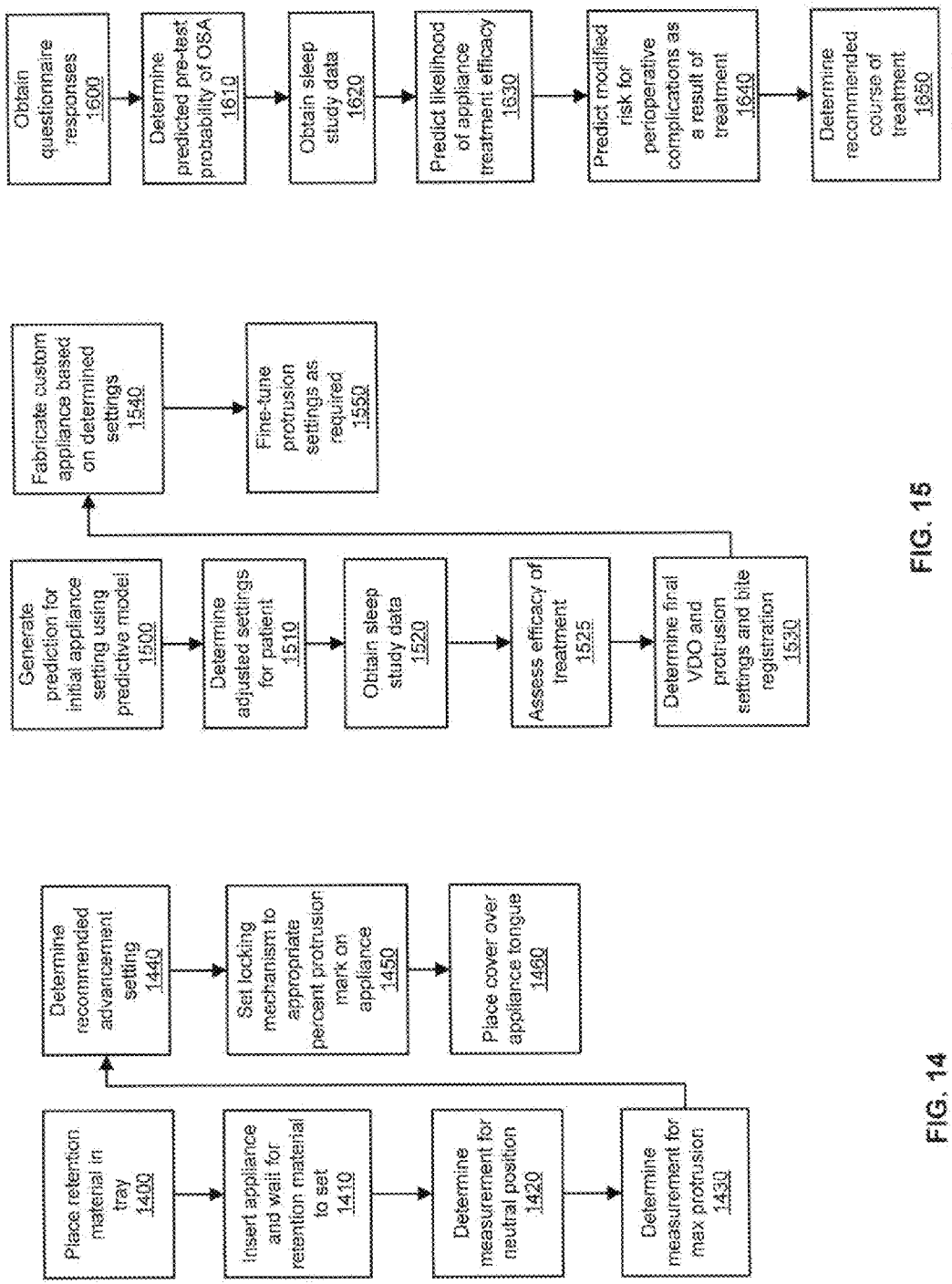

Table 1. Correlations between Post-Treatment AHI and Pre-treatment Variables

| | Post-treatment AHI | | | | Post-treatment RDI | | | |
|---|---|---|---|---|---|---|---|---|
| | Males | | Females | | Males | | Females | |
| | Pearson r | p ≤ | Pearson r | p ≤ | Pearson r | p ≤ | Pearson r | p ≤ |
| AHI | 0.53 | 0.0001 | 0.42 | 0.01 | 0.46 | 0.0001 | 0.45 | 0.01 |
| RDI | 0.55 | 0.0001 | 0.40 | 0.05 | 0.58 | 0.0001 | 0.47 | 0.01 |
| AHI Supine | 0.48 | 0.0001 | 0.10 | NS | 0.47 | 0.0001 | 0.11 | NS |
| RDI Supine | 0.42 | 0.0001 | 0.08 | NS | 0.51 | 0.0001 | 0.12 | NS |
| AHI Non-supine (l) | 0.52 | 0.0001 | 0.53 | 0.001 | 0.54 | 0.0001 | 0.57 | 0.001 |
| RDI Non-supine (l) | 0.46 | 0.0001 | 0.53 | 0.001 | 0.57 | 0.0001 | 0.64 | 0.0001 |
| AHI Sup/Non-Sup ratio (l) | -0.19 | NS | -0.40 | 0.05 | -0.13 | NS | -0.39 | 0.05 |
| % time SpO2 < 90% | 0.39 | 0.001 | 0.48 | 0.01 | 0.29 | 0.01 | 0.43 | 0.01 |
| Snoring > 30 dB | 0.30 | 0.01 | 0.19 | NS | 0.40 | 0.001 | 0.23 | NS |
| Snoring > 40 dB | 0.27 | 0.05 | 0.20 | NS | 0.39 | 0.001 | 0.14 | NS |
| BMI (l) | 0.29 | 0.01 | 0.43 | 0.01 | 0.30 | 0.01 | 0.39 | 0.05 |
| Neck size | 0.19 | NS | 0.44 | 0.01 | 0.28 | 0.01 | 0.47 | 0.01 |
| Epworth | 0.15 | NS | -0.39 | 0.05 | 0.04 | NA | -0.41 | 0.01 |

(l) = logged

FIG. 18

Table 2: Table for Selecting an Oral Appliance that Optimizes Outcomes

| Tongue Size | Sleeps Supine ≥ 40% of night | Sleeps Supine < 40% of night |
|---|---|---|
| Males | | |
| Normal | VDO High (e.g., 8.5 mm) | VDO Medium (e.g., 6.5 mm) |
| Scalloped | VDO High | VDO High |
| Females | | |
| Normal | VDO Medium | VDO Low (e.g., 5.5 mm) |
| Scalloped | VDO High | Medium |

FIG. 19

| Inter-Tray Height | Tray Marking | | Vertical Dimension |
|---|---|---|---|
| | Upper | Lower | |
| Low | L | L | 5.0 mm |
| Medium | L | H | 6.7 mm |
| High | H | H | 8.5 mm |

FIG. 24

SYSTEMS AND METHODS FOR OPTIMIZING ORAL APPLIANCE THERAPY FOR THE TREATMENT OF SLEEP APNEA

RELATED APPLICATION

This application claims the benefit of U.S. provisional patent application Ser. No. 61/318,111, entitled "SYSTEM FOR PREDICTING OUTCOMES AND OPTIMIZING THE TREATMENT OF SLEEP APNEA," filed on Mar. 26, 2010, which is incorporated herein by reference in its entirety.

FIELD OF THE INVENTION

The systems and method disclosed herein generally relates to the field of treating obstructive sleep apnea and to systems and methods for managing therapeutic outcomes using oral appliance therapy to reduce sleep apnea severity.

BACKGROUND

The prevalence of obstructive sleep apnea (OSA) in adults in Western countries is growing at an exponential rate, with as many as 50% of middle-aged males and 20% of middle-aged females have at least mild sleep disordered breathing. OSA is characterized by periodic, partial or complete obstruction of the upper airway during sleep. The underlying pathophysiology of OSA is complex. However, it is generally accepted that the stability and patency of the upper airway is dependent upon the action of oropharyngeal dilator muscles which are normally activate during inspiration. These muscles increase activity to overcome obstruction during wakefulness, but the normal decrease in activity that occurs during sleep leaves the airway susceptible to collapse. Return of airway muscle activity requires either an arousal or a change of brain state to a lighter stage of sleep. Given the choice between sleeping and breathing, the un-medicated brain will choose breathing. The repetitive asphyxia causes repetitive arousals which fragments sleep and causes daytime somnolence. Airway obstruction also causes sleep-associated oxygen desaturation, episodic hypercarbia, and cardiovascular dysfunction.

The most common method used to treat OSA is through the application of continuous positive airway pressure (CPAP). An alternative approach, called oral appliance therapy (OAT), protrudes the mandible in a forward position thereby reducing obstruction during sleep caused by the tongue and linked soft tissues. OAT is considered limited when compared to CPAP because it is not effective in all patients. Efficacious OAT outcomes is dependent on a number of factors, including but not limited to a patient's gender, supine and non-supine OSA severity, age, body mass index, neck size and the anatomical source/region of obstruction. Successful outcomes are also influenced by two factors which should be combined to improve outcomes for any given patient. The first factor to consider is degree of protrusion, measured by the distance between a natural biting position and maximum protrusive jaw effort. Conventional practice is to advance the mandible between 60% to 80% of maximum voluntary protrusion. The second factor is the vertical dimension of occlusion (VDO) that can be incorporated into the oral appliance. To promote comfort, the VDO (space between the upper and lower teeth while protruding) is commonly reduced so the patient can achieve a good lip seal when the appliance is inserted. Limiting the vertical dimension between the upper and lower tray, however, reduces space in the oral cavity for the tongue to advance. This is particularly a problem in patients with large or scalloped tongues or those who sleep predominantly supine. FIG. 22 illustrates an example of a human tongue that exhibits scalloping along the edge of the tongue (2200). In comparison, FIG. 23 illustrates an example of a human tongue that does not exhibit scalloping along the edge. Increasing the VDO expands the space available for the genioglossus to advance and reduces the amount of protrusion needed for treatment efficacy. Optimally combining protrusion and VDO decreases the impact of OAT on bite change, the temporomandibular joint and associated muscle pain.

Oral appliances are typically fabricated by dental laboratories and made from materials which provide for two or more years of useful life. Fabrication of a custom appliance is dependent on a dentist providing impressions taken from the patient's upper and lower teeth as well as a bite registration for aligning the upper and lower teeth in the final appliance. Depending on the appliance, sub-millimeter protrusion adjustment can be attained based on thread pattern in order to extend the lower tray (teeth) beyond the upper tray (teeth). Because screw length and thread count limit the advancement range, the dentist is required to select a starting setting for the patient/appliance so that presumably the optimal advancement can be obtained without the need for appliance rework (i.e., removal and shifting of the adjustment mechanism to a more forward position to increase the protrusion range). Alternative protrusion methods include use of elastic bands to advance the lower tray, or inter-connecting slots where the upper (lower) trays fits into a limited number of advancement slots in the lower (upper) tray. These methods typically provide more limited options as to the number of advancement setting.

Appliances that do not provide advancement resolution of at least 1 mm tend to be less efficacious. A lack of advancement precision makes it difficult to select a starting setting that minimizes muscular pain causes by the initiation of nocturnal advancement. Limited incremental advancement also decreases the likelihood that an end point setting can be selected that optimizes therapeutic outcomes while also minimizing advancement that contributes to long term side effects (i.e., tooth movement, mandible repositioning, etc.)

Non-custom appliances are typically fitted to the teeth after modification to the material, e.g., thermal heating of a boil-and-bite appliance. Non-custom appliances can also be made with impression material to secure the teeth to the appliance, however, the limited life of the impression material (e.g., 30 days or less) suggest that these appliances are temporary in nature. Most non-custom or temporary appliances utilize low resolution protrusion methods.

Given the teeth are used to secure the OAT in place and the forces needed to advance the mandible are applied directly to the teeth, good periodontal health and dental hygiene is necessary for long term OAT use. Custom appliances have a smaller impact, while non-custom or boil-and-bite devices have a relatively greater impact on dental morbidity. The trays used to fabricate a non-custom oral appliance must either be manufactured in a range of sizes or be adjustable to accommodate the range of human dental arch widths. If the appliance does not properly accommodate arch width, the edges of the upper or lower tray will rub against the gums and cause discomfort or the appliance will be painful to wear for extended periods. It is not uncommon for patients who have snoring or OSA to clench and grind their teeth. Thus, oral appliances intended for sleep apnea patients should be designed to accommodate the forces applied by the clenching (bruxing) of the upper and lower teeth.

As mentioned previously, optimal OAT outcomes are dependent on combining protrusion with VDO. However, the VDO is not easily adjustable in many custom oral appliances once fabricated. Thus, it would be beneficial to determine the optimal oral appliance settings prior to the fabrication of a custom appliance. Providing a means for a physician to inexpensively conduct a trial and determine whether a patient responds to OAT prior to the fabrication of a custom appliance would also be beneficial. Providing a means whereby the determined oral appliance settings used in the trial that resulted in an efficacious outcome may be transferred to the custom appliance would also be beneficial.

Management of sleep disordered breathing present special perioperative challenges in patients due to the increased likelihood of respiratory depression and hypoxemia following surgery. Anesthesia, analgesia, and sedation drugs, commonly administered during and post-surgery and the recovery period, increase the severity of sleep disordered breathing by inhibiting the brain's capability to respond to obstructive breathing related hypoxemia or compromising the patency of the oropharyngeal dilator muscles. During initial recovery from general anesthesia, patients are nursed on their back and carefully monitored in the post-anesthetic recovery unit (PACU) until their self-supported ventilation and vital signs stabilize. Immediately following extubation and for the next few hours it is not uncommon for staff to manually advance the mandible forward (i.e., chinning) to keep the airway open in patients with obstructive sleep apnea.

Once patients leave the PACU the perioperative risks associated with obstructive breathing remain high due to the high levels of pain that mandate administration of analgesics (especially opioids) and changes in patterns of sleep architecture. REM-associated hypoxemic episodes is thought to increase about three-fold on the second and third postoperative nights. The rebound of slow wave sleep raises the arousal threshold, prolonging the time to arousal and allowing longer episodes of obstruction with deeper oxyhemoglobin desaturations. Because patients are routinely nursed on their hack, and gravity contributes to increased retrusion of the tongue and collapsibility of the airway, the incidence of obstructive breathing and severity of associated hypoxemia is increased independent of sleep stage. Even if supplemental oxygen is administered to reduce hypoxic exposure during obstructive breathing events, the physiological effects of repeated arousals (tachycardia and increased arterial blood pressure) add to the risk of perioperative complications. Because oxygen therapy and critical oxyhemoglobin saturation monitoring is generally discontinued prior to the REM-rebound, the highest perioperative mortality risk is not the day of surgery, or even the second day; it is on the third or fourth postoperative day. These risks continue in discharged patients who remain on narcotic pain medication. The most severe adverse outcome resulting from undiagnosed OSA is that the patient dies or becomes brain dead, the more common outcome is increased patient care cost resulting from complications that increase the length of the hospital stay or amount of time spent in the PACU or in critical care.

The American Society of Anesthesiologists recommends that all patients scheduled for general anesthesia be screened for undiagnosed OSA. One study estimated over 40% of those scheduled for general anesthesia have undiagnosed OSA based on a predictive analysis of questionnaire responses and overnight sleep study data. Thus, the feasibility for screening and potentially diagnosing patients with OSA prior to surgery was established. What has yet to be resolved is how to identify patients likely to have severe OSA and then how to mitigate OSA perioperative risk. Because most patients are unable to tolerate CPAP therapy when it is introduced post-operatively, for CPAP to be an effective perioperative intervention, patients must be identified a-priori and undergone a CPAP trial prior to admission. In most cases, this is simply not feasible. Given the risk of perioperative complications for those with untreated OSA and the ageing of the population it's likely the number of OSA-related adverse events will increasingly become a safety concern. Thus, an oral appliance that can be easily fitted and designed to manage the treatment of sleep apnea in a perioperative setting would be beneficial.

SUMMARY

Systems and methods are provided herein for optimizing the treatment of obstructive sleep apnea (OSA) using an oral appliance. A configurable oral appliance is provided that can be configured by non-dental staff to safely conform to the dentition of a patient. The appliance includes configurable trays that include retention material that conforms to the dentition of the patient. The position of the upper and lower trays relative to one another can be adjusted both horizontally and vertically. The position of the upper and lower trays can be locked into place to maintain the position of the trays at a preferred treatment position. Methods for creating an appliance customized for a patient are also provided. Methods for using the oral appliance in combination with sleep study data is also provide. Methods for using the oral appliance in combination with pre-operative assessments and sleep study data to predict and reduce the risk of perioperative complications are also provided.

According to an embodiment, an oral appliance for treating obstructive sleep apnea of a patient through maintaining a position of the patient's upper jaw relative to a position of the patient's lower jaw is provided. The appliance includes a removable upper tray configured to affix to a patient's upper teeth. The appliance also includes an upper tongue portion extending outwardly from the upper tray. The appliance also includes a lower tray configured to removably affix to the patient's lower teeth, and a lower tongue portion extending outwardly from the lower tray. The upper tongue portion and the lower tongue portion are designed to engage and slide with each other, limiting motion of the upper tray relative to the lower tray to a longer common axis of the upper tongue portion and the lower tongue portion. The appliance also includes a plurality of locking holes located on the upper tongue portion and the lower tongue portion, and a locking mechanism having at least one locking post configured to extend through a locking hole on the upper tongue portion and a locking hole on the lower tongue portion when the two holes are aligned and thereby fix a position of the upper tray relative to the lower tray.

According to another embodiment, a method for creating a oral appliance for treating obstructive sleep apnea (OSA) is provided where the appliance maintains a position of a patient's upper jaw relative to a position of the patient's lower jaw to facilitate breathing while the patient is asleep and the appliance includes an upper tray configured to removably affix to the patient's upper teeth and a lower tray configured to removably affix to the patient's lower teeth. The method includes the steps of placing an uncured retention material in an upper tray and a lower tray of the appliance, the retention material being a non-toxic material for capturing dental impressions, insert the appliance into the patient's mouth before the retention material cures, wait for the retention material to set while the patient bites down on the retention material, determine measurement for neutral position setting for the appliance while the patient maintains a neutral occlusal position of the upper and lower jaws, determine measurement for maximum protrusion setting for the appliance while the patient extends the lower jaw as forward as far as possible without assistance, determine recommended protrusion setting based on neutral position measurement and maximum protrusion measurement, and setting a locking mechanism on the appliance to fix a position of the upper tray relative to the lower tray at one of a plurality of protrusion settings to maintain the position of the patient's upper and lower jaws at a fixed relative position while the patient is wearing the appliance.

According to another embodiment, method for treating obstructive sleep apnea (OSA) using a removable oral appliance and sleep studies to determine and optimize the efficacy of the treatment is provided where the appliance maintains a position of a patient's upper jaw relative to a position of the patient's lower jaw to facilitate breathing while the patient is asleep. The appliance includes an upper tray configured to removably affix to the patient's upper teeth and a lower tray configured to removably affix to the patient's lower teeth. The method includes the steps of generating a prediction for initial appliance settings for a temporary appliance using predictive model, determining adjusted appliance settings for patient based on measurements taken while the patient is wearing a temporary appliance, collecting sleep study data while the patient is wearing the temporary appliance set to the adjusted appliance setting, the sleep study data including physiologic data monitoring physiologic parameters of the patient indicative of OSA symptoms, analyzing the sleep study data to determine an efficacy assessment for the temporary appliance, adjusting the appliance settings based on the efficacy assessment to create modified appliance settings, and fabricating a custom appliance for the patient based on the modified appliance settings of the temporary appliance.

According to another embodiment, a method for treating obstructive sleep apnea (OSA) using a removable custom appliance and sleep studies to determine the efficacy of the treatment is provided where the appliance maintains a position of a patient's upper jaw relative to a position of the patient's lower jaw to facilitate breathing while the patient is asleep. The appliance includes an upper tray configured to removably affix to the patient's upper teeth and a lower tray configured to removably affix to the patient's lower teeth. The method includes the steps of collecting responses to an OSA assessment questionnaire from the patient, determining a pretest probability of the patient having OSA based on the collected responses, collecting sleep study for the patient, the sleep study data including physiologic data monitoring physiologic parameters of the patient indicative of OSA symptoms, analyzing the sleep study data to determine a predicted treatment efficacy of treating patient using custom oral appliance, predicting modified risk for perioperative complications for the patient based on the predicted treatment efficacy, and determining a recommended course of treatment for the patient based on the predicted modified risk of perioperative complications.

BRIEF DESCRIPTION OF THE DRAWINGS

The details of the present invention, both as to its structure and operation, may be gleaned in part by study of the accompanying drawings, in which like reference numerals refer to like parts, and in which:

FIG. 11 provides an example of a lookup table that can be used to look up a recommended advancement setting for the appliance illustrated in FIGS. 1-10 based on neutral and maximum position settings determined while the patient is wearing the appliance;

FIG. 14 is a flow diagram of a method that can be used to prepare the appliance illustrated in FIGS. 1-13 for use with a patient according to one embodiment;

FIG. 15 is a flow diagram of a process for utilizing the appliance disclosed in the FIGS. 1-13 in sleep centers that diagnose and/or treat sleep-related disorders according to an embodiment;

FIG. 16 is a flow diagram of a process for utilizing the appliance disclosed in the FIGS. 1-13 in medical delivery model according to an embodiment;

FIG. 18 is a table illustrating correlations between post-treatment AHI and pre-treatment variables;

FIG. 19 is a table that can be used to select an appropriate oral appliance to optimize the outcome for male and female patients according to an embodiment;

FIG. 24 is a table illustrating how trays of different heights can be used to provide different VDOs for a patient.

DETAILED DESCRIPTION

Systems and methods are provided herein for optimizing the treatment of obstructive sleep apnea (OSA) using an oral appliance. A configurable oral appliance is provided that can be configured by non-dental staff to safely conform to the dentition of a patient. The appliance includes configurable trays that include retention material that conforms to the dentition of the patient. The position of the upper and lower trays relative to one another can be adjusted both horizontally and vertically. The position of the upper and lower trays can be locked into place to maintain the position of the trays at a preferred treatment position. Methods for creating an appliance customized for a patient are also provided.

In some embodiments, the configurable oral appliance disclosed herein can be used in combination with sleep studies to determine a set of settings that optimize the efficacy of the treatment of a patient's OSA. The set of settings can then be used to fabricate a custom oral appliance that is specifically configured for that particular patient.

In some embodiments, the configurable oral appliance disclosed herein can also be used in combination with OSA risk assessment questionnaires and sleep study data to determine predict and reduce the risk of perioperative complications that a patient may experience.

Figure 1:
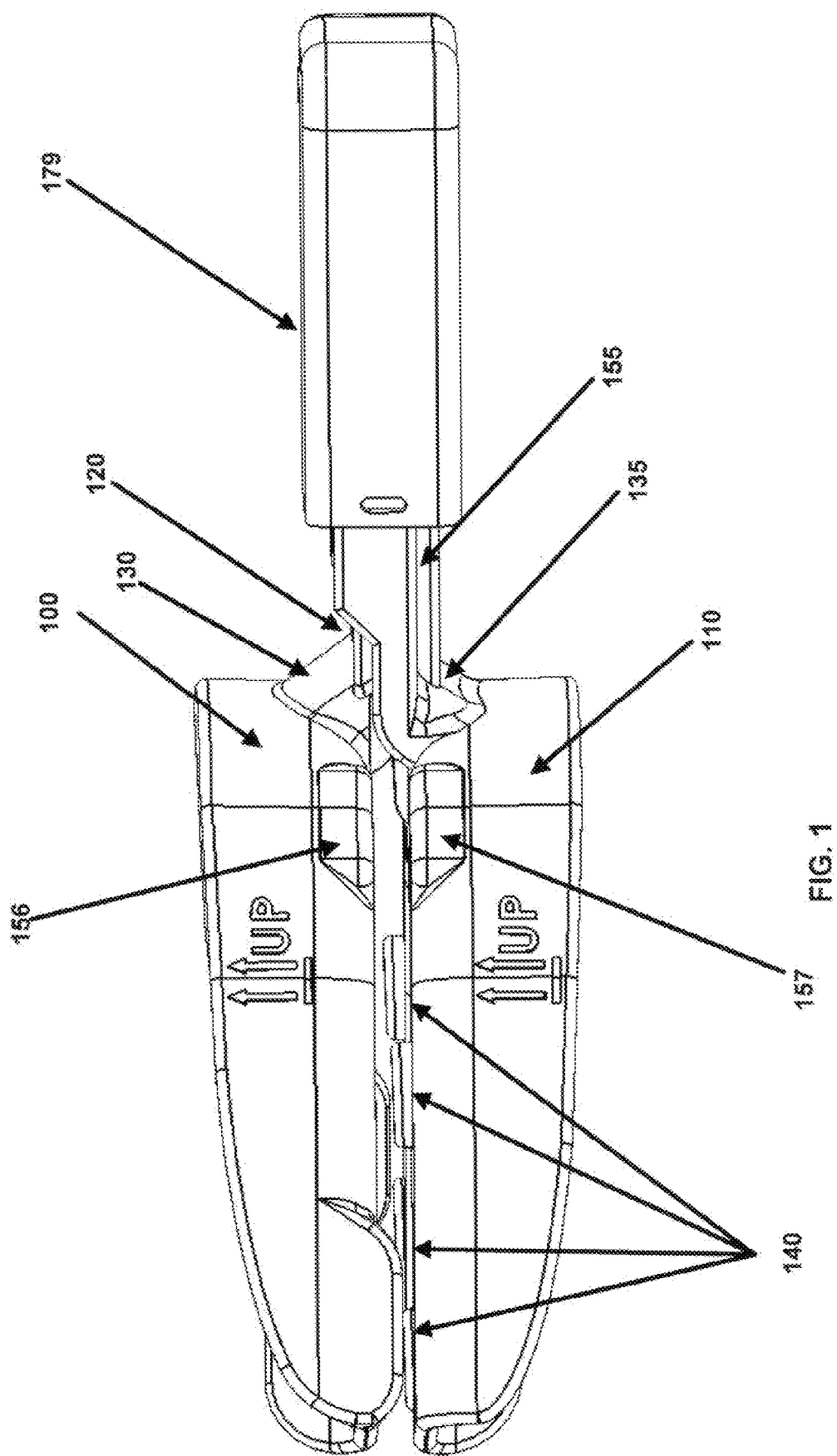
FIG. 1 is a side view of an example of an oral appliance that can be used to optimizing the efficacy of oral appliance therapy in the treatment of OSA according to an embodiment.

FIG. 1 illustrates an example of an oral appliance that can be used to optimize the efficacy of oral appliance therapy in the treatment of obstructive sleep apnea according to an embodiment. FIG. 1 illustrates an oral appliance comprising an upper portion that comprises an upper tray 100 and an upper tongue portion 150 (obscured in FIG. 1, but visible in FIGS. 3 and 4). The upper tongue portion 150 extending outwardly from the upper tray 100. The oral appliance also includes a lower portion that comprises a lower tray 110 and a lower tongue portion 155. The lower tongue portion 155 extending outwardly from the lower tray 110. The upper tongue portion 150 of the upper tray 100 can be inserted into the lower tongue portion 155 of a lower tray 110 at insertion point 120. The upper tongue portion 150 and the lower tongue portion 155 slidably engage with each other limiting motion of the upper tray 100 relative to the lower tray 110 to a longer common axis of the upper tongue portion 150 and the lower tongue portion 155. One skilled in the art will recognize that any number of shapes of the tongue portions of the upper and lower tray can be used and that while the figures provided herein ill, a curved shape can be used in other embodiments.

In the embodiment illustrated in FIG. 1, the lower tongue portion 155 is partially obscured by a tongue cover 179. According to an embodiment, the lower tongue portion 155 has grossly U-shaped cross-section into which the upper tongue portion 150 can be inserted. The U-shaped cross section of lower tongue portion 155 can be seen at least in FIG. 2. One skilled in the art will recognize that the shapes of the upper and lower tongue portions can vary and that shape that allow the upper and lower tongue portions to slidably engage with one another can be used in other embodiments.

Figure 10:
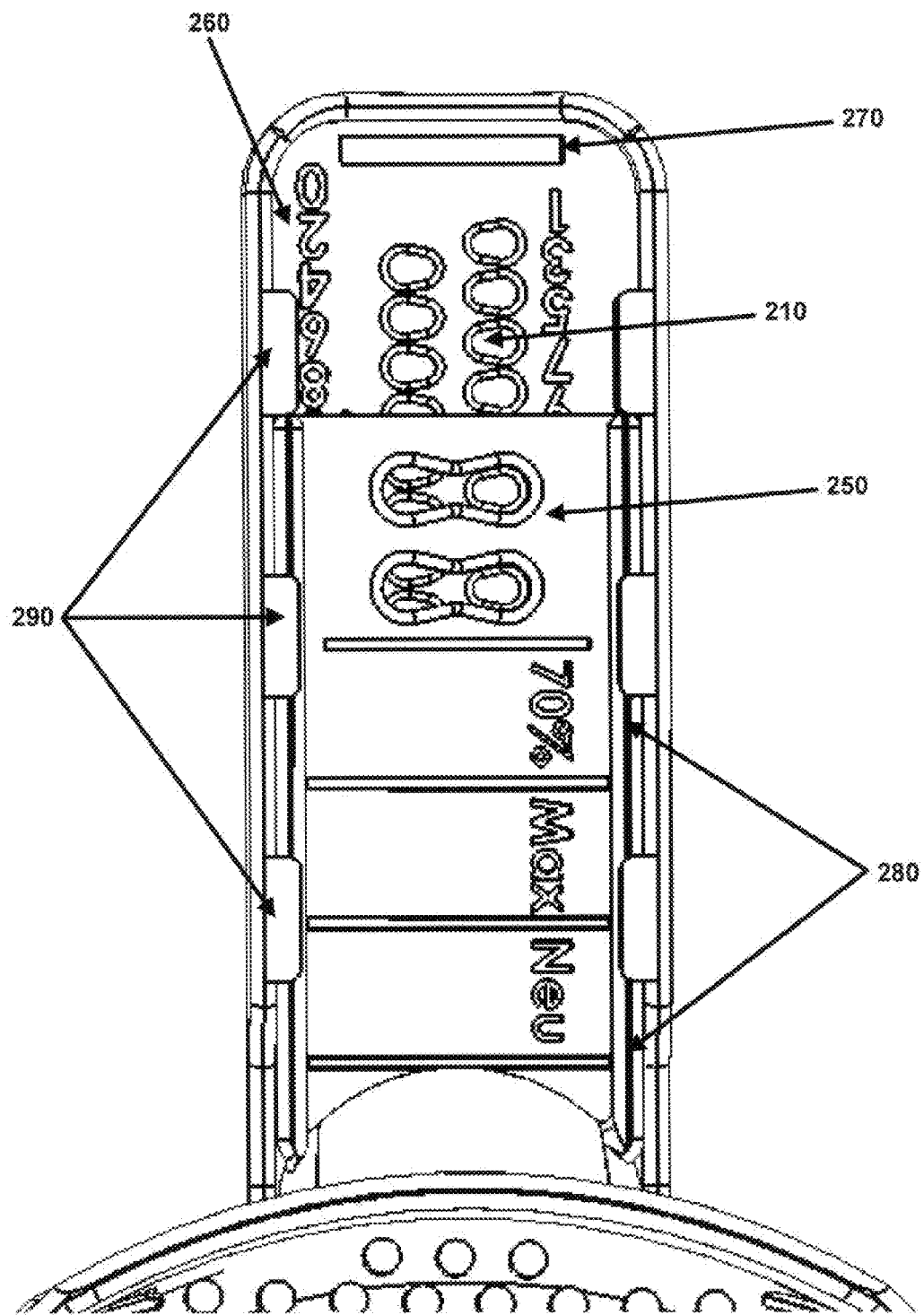
FIG. 10 presents a top view of the appliance tongue showing how the upper and lower trays interface and how the user can read and mark the adjustment settings according to an embodiment.

According to an embodiment, the upper tongue portion 150 of the upper tray 100 slides along retaining members in the lower tray 110 to allow anterior and posterior adjustment of the upper tray 100 relative to the lower tray 110. In FIG. 1, the retaining members are obscured by cover 179. However, FIG. 10 illustrates an embodiment of the appliance where the retaining members 290 are visible. In other words, the upper tray 100 can be slid toward the posterior of a patient's mouth relative to the lower tray 110, or the upper tray 1100 can be slid toward the anterior of the patient's mouth relative to the lower tray 110. The height (in the vertical dimension of FIG. 1) of the tray necks 130 and 135 of the upper and lower trays can be adjusted to provide a range of vertical dimension of occlusions (VDO) for the appliance. Thicker tray necks 130 and 135 can be used to increase the vertical displacement of the trays.

According to an embodiment, the height (in the vertical dimension of FIG. 1) of the posterior bite posts 140 corresponds to the VDO provided by the tray necks. In a preferred embodiment, multiple posterior bite posts can be used to provide adequate support for the full range of adjustments provided by the oral appliance. In another embodiment, the height of the bite posts 140 can be adjusted with two interthreaded components.

FIG. 24 is a table illustrating how trays of different heights can be combined to provide different VDOs for a patient. In some embodiments, medical practitioners can select from a set of upper and lower trays that have a range of VDO settings associated with them. For example, if a smaller (or low) VDO is required, an upper tray and a lower tray that both have a "low" VDO can be selected. In the embodiment illustrated in FIG. 25, the combination of and upper and lower tray that both have a low VDO setting results in a vertical displacement of 5.0 mm for the two trays combined. As can be seen from the table of FIG. 25, other combinations of trays can be used to provide other vertical displacements. While the embodiment illustrated in FIG. 25 merely includes a range of three possible size each for the upper and lower trays, other embodiments can include a wider range of VDO settings that allow for even greater fine tuning of the VDO settings.

Returning now to the embodiment illustrated in FIG. 1, the radial edge design of the upper neck 130 of the upper tray 100 and the lower neck 135 of the lower tray 110 at the intersection with the upper tray 100 and the lower tray 110 provide soft tissue comfort. The radial edge design can make the device more comfortable on the lips and tongue of a patient using the appliance.

In a preferred embodiment, the mating and relative positioning of the upper and lower trays occur at the upper tongue portion 150 of the upper tray 100 and the lower tongue portion 155 of the lower tray 110. The upper tongue portion 150 and the lower tongue portion 155 extend from the patient's mouth during use. Extending the appliance tongues outside of the patient's mouth allows the appliance to be readily removed by hospital staff and maximizes tongue space within the oral cavity for the patient's tongue. According to an embodiment, a silicone cover 179 can be applied over the upper and lower tongues to conceal the appliance's adjustment features, to protect the locking mechanism, and/or to provide aesthetic benefit.

Figure 2:
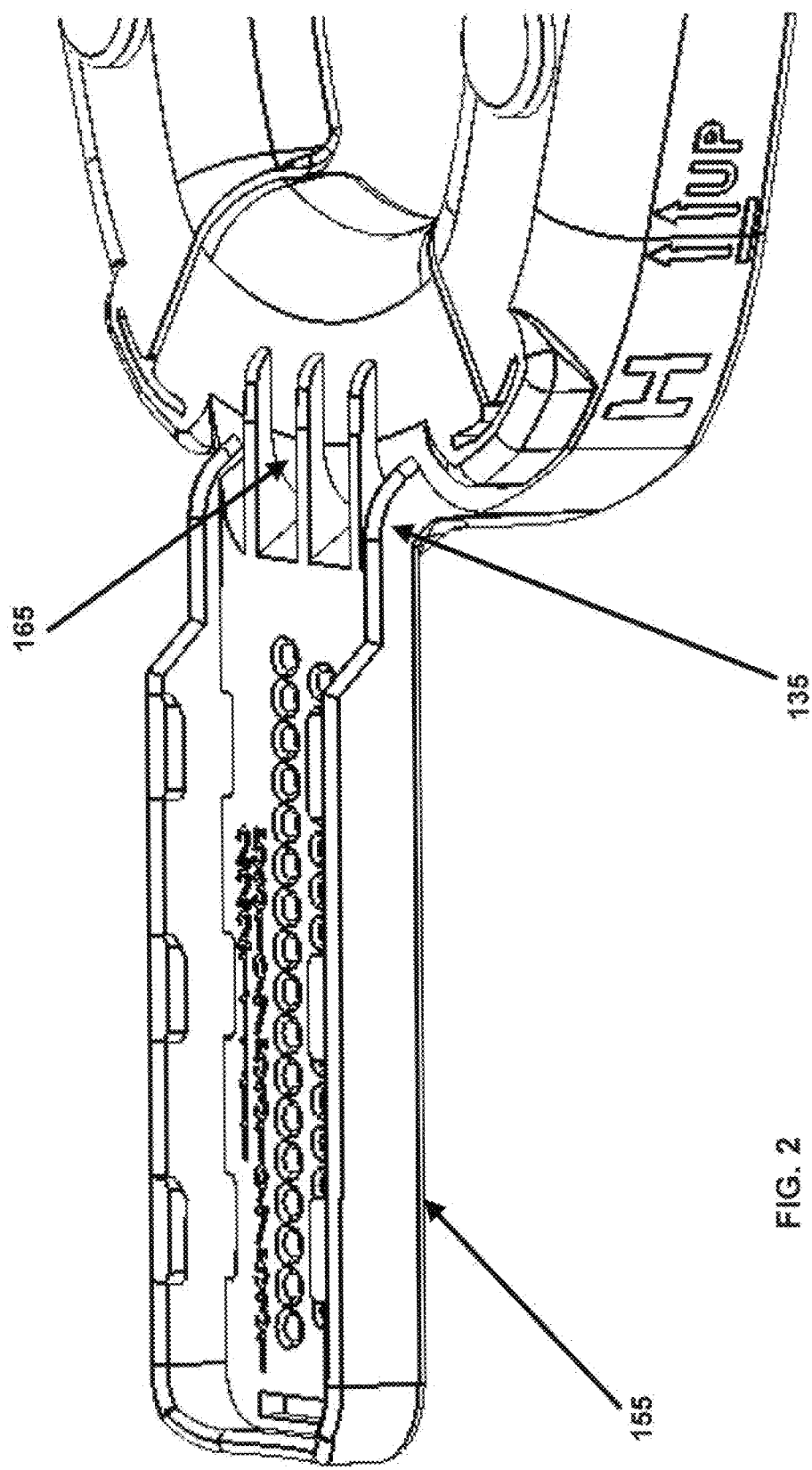
FIG. 2 is a detailed view of a portion of the lower tray of the appliance illustrated in FIG. 1 according to an embodiment.

FIG. 2 illustrates a view of the lower tray 110 of the appliance illustrated in FIG. 1 according to an embodiment. The embodiment illustrated in FIG. 2 illustrates one embodiment of the lower tray 110 where the VDO of the appliance can be adjusted on the lower tray. The neck 135 of the lower tongue portion 155 is extended upward and further comprises conjoined ribs 165 to provide support for the upper tray 100 across the full range of protrusion settings. As described above, the thickness tray neck 135 of the lower tray 110 and the neck 130 of the upper tray 100 can be adjusted to provide a range of VDOs for the appliance.

Figure 3:
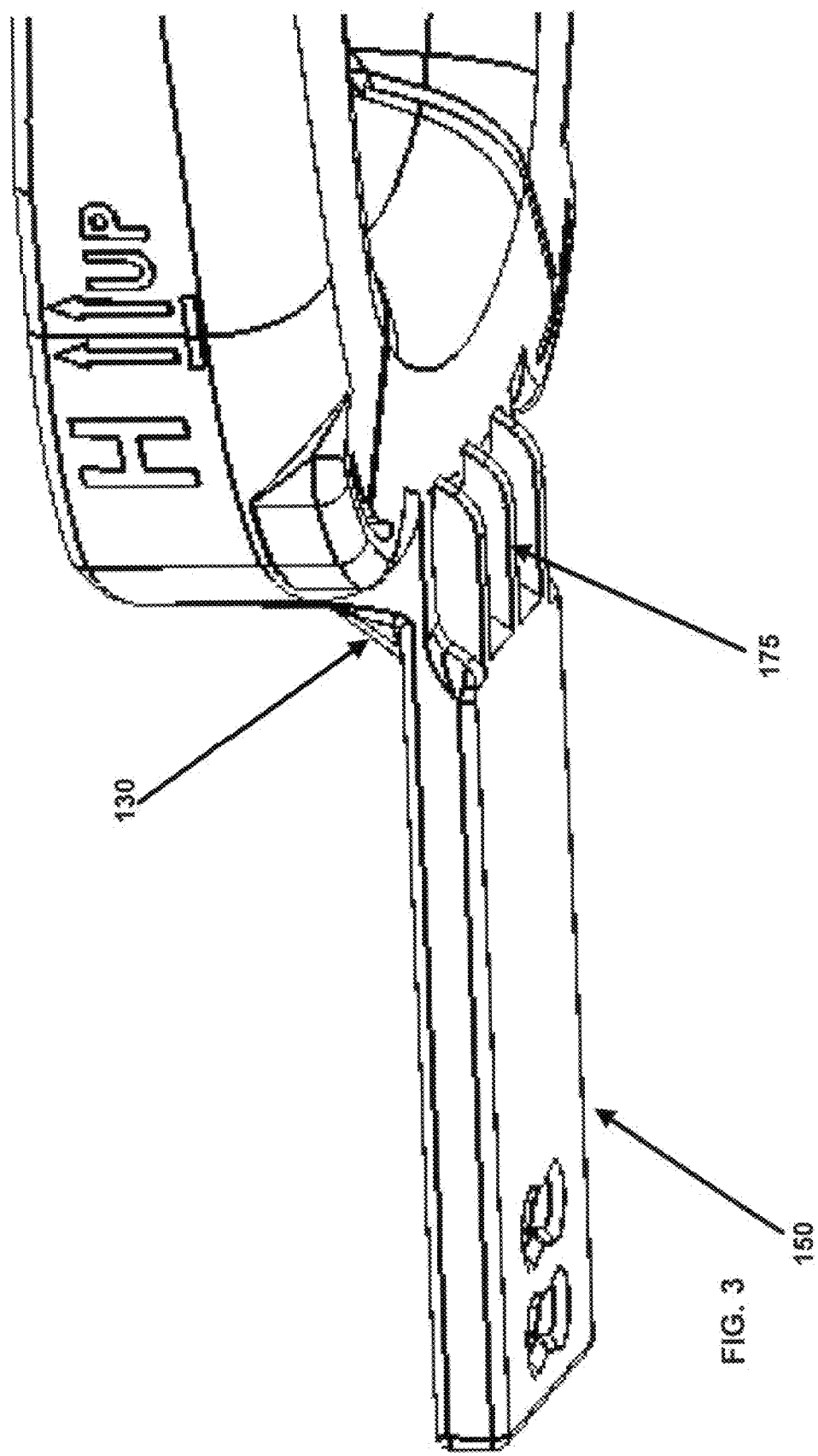
FIG. 3 is a detailed view of a portion of the upper tray of the appliance illustrated in FIG. 1 according to an embodiment.

FIG. 3 illustrates a view of the upper tray 100 of the appliance illustrated in FIG. 1 according to an embodiment. The neck 130 and the ribs 175 of the upper tray 100 provide increased VDO for the appliance by including a thicker neck and ribs. The height (in the vertical dimension of FIG. 1) of the tray neck 130 and of ribs 175 of the upper tray 100 can be adjusted to provide a range of vertical dimension of occlusions (VDO) for the appliance. As described above, the height of the neck 135 and ribs 165 of the lower tray 110 can also be adjusted in addition to or instead of the height of the tray neck 130 and ribs 175 of the upper tray 100.

Figure 4:
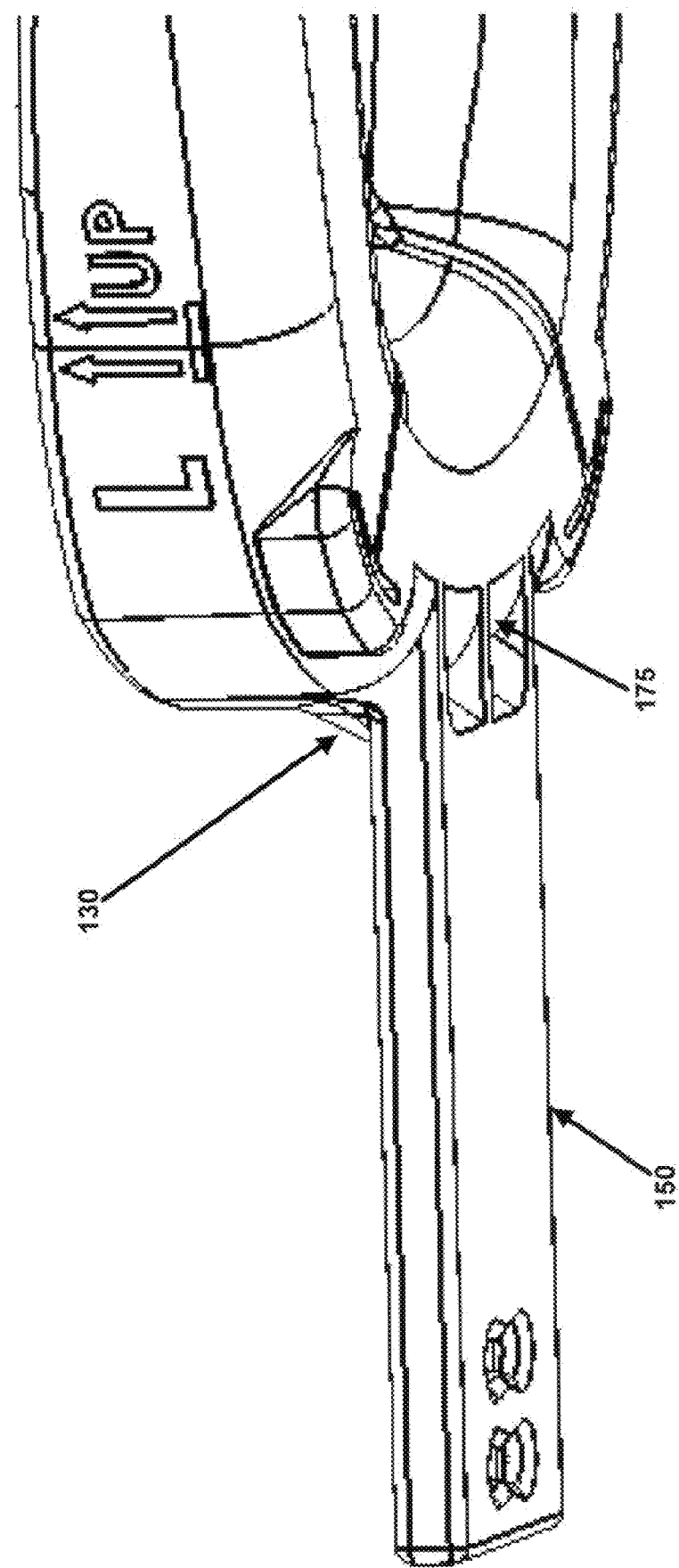
FIG. 4 illustrates a view of the upper tray that provides more limited vertical dimension of occlusion (VDO) than the embodiment illustrated in FIG. 3 according to an embodiment.

FIG. 4 illustrates a view of the upper tray 100 that provides less VDO than the embodiment illustrated in FIG. 3 according to an embodiment. In the embodiment of FIG. 4, the upper tray 100 provide more limited VDO because the neck 130 does not include an extension as does the neck 130 of the embodiment illustrated in FIG. 3. The ribs 175 of the embodiment illustrated in FIG. 4 are also in line with the lower edge of the upper tray 100. One skilled in the art will recognize a range of VDO options can be derived by pairing different combinations of upper and lower neck and rib dimensions and/or utilizing different approaches that change the relationship between the tongue portion and the tray that seats the teeth in the upper and/or lower portions of the appliance.

Figure 5:
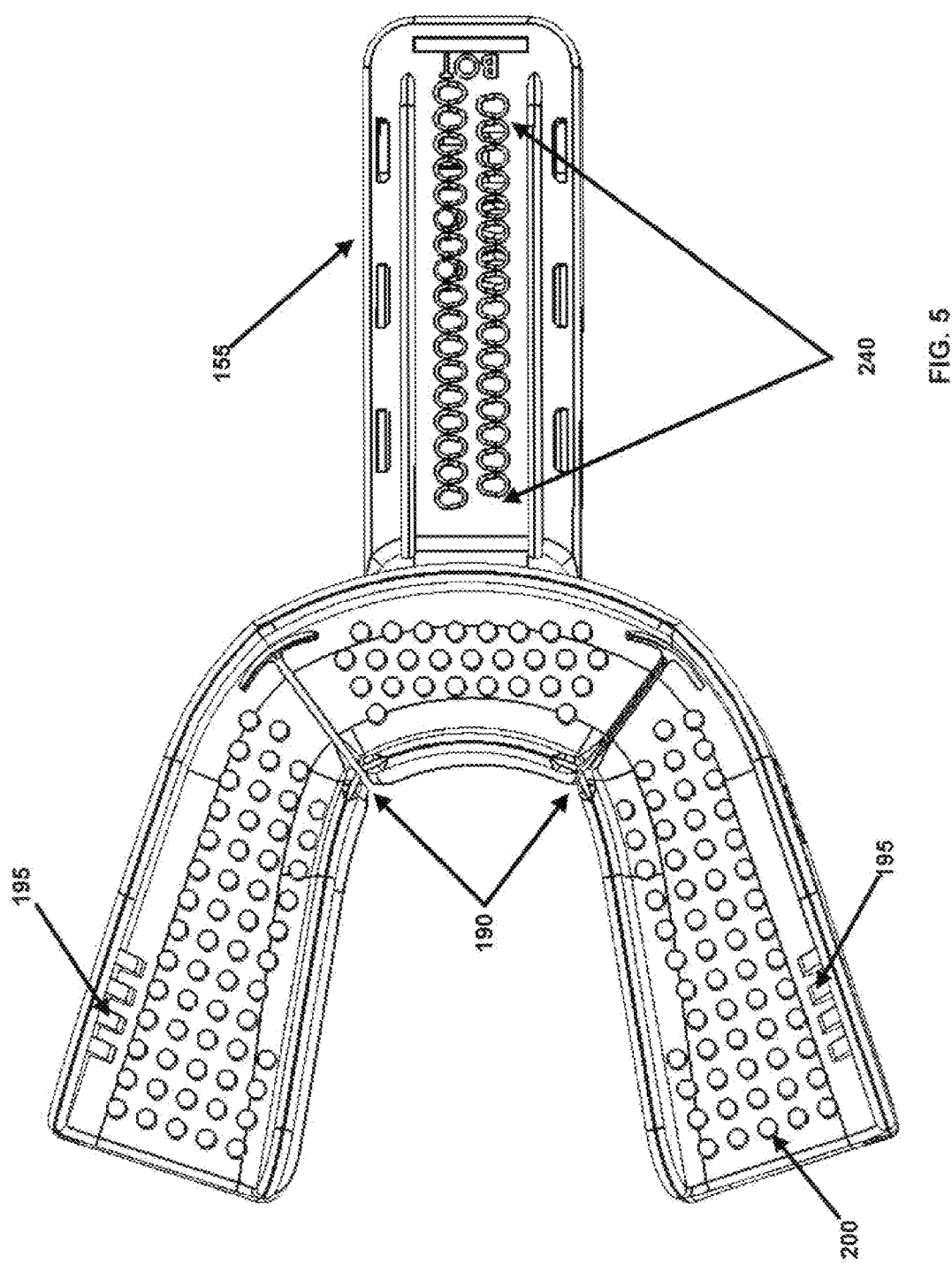
FIG. 5 illustrates a view of the underside of the lower tray illustrated in FIG. 1 according to an embodiment.

FIG. 5 illustrates a view of the underside of the lower tray 110 illustrated in FIG. 1 according to an embodiment. Bi-directional slots 190 in the bottom aspects of the tray(s) provide allow for the width of the trays to adjust, allowing a single size tray to accommodate a full range of dental arch types. According to an embodiment, the width and length of the bi-directional slots 190 can be limited to avoid retention material from extruding and inadvertently bonding the upper tray 100 and lower tray 110 while the retention material is being used to take an impression of the patient's teeth.

Figure 20:
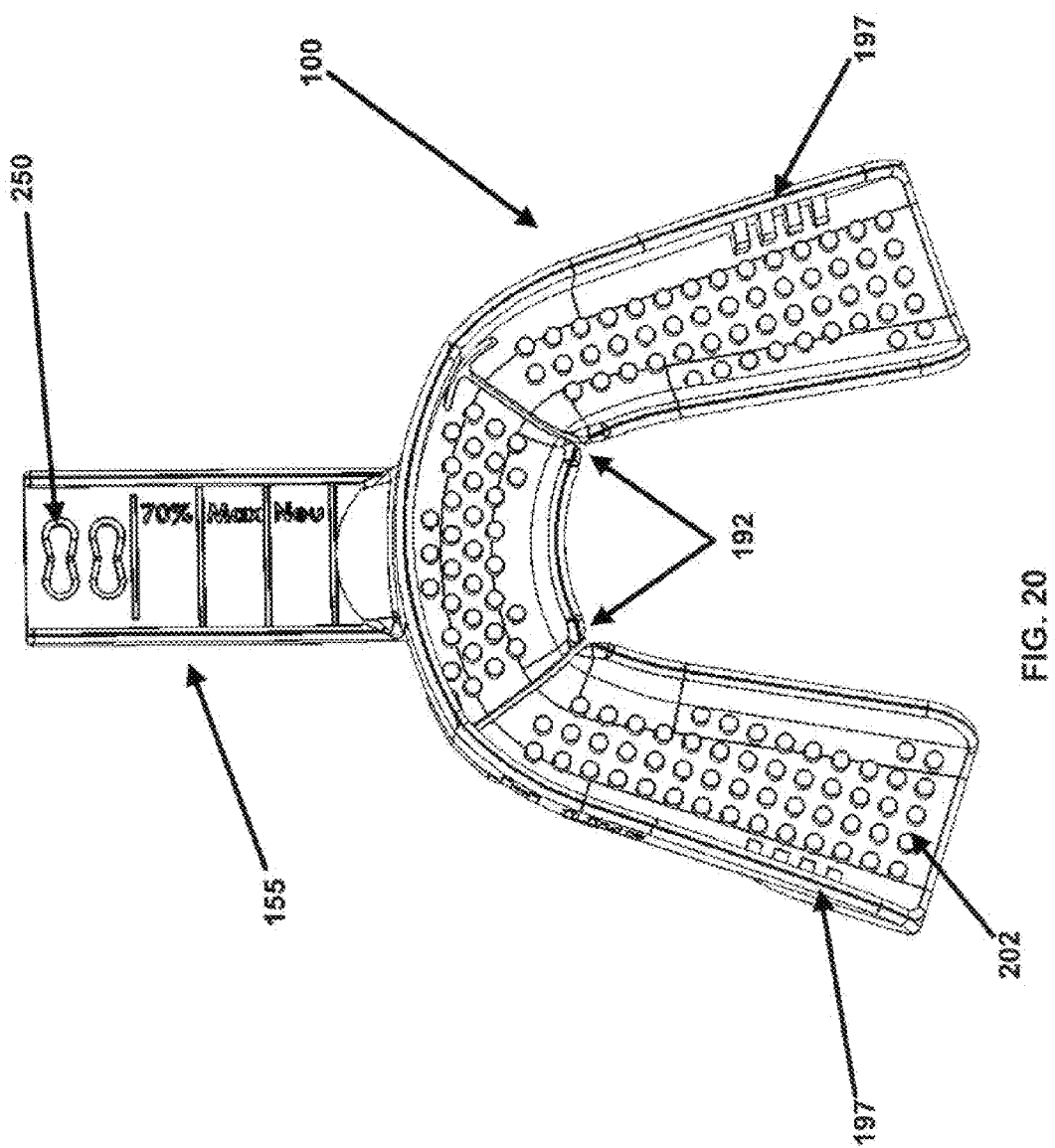
FIG. 20 illustrates a top view of the upper tray and upper tongue portion of the appliance according to an embodiment.

According to an embodiment, the lower tray 110 can include protection walls 157 (shown FIG. 1) that in combination with the bi-directional slots 190 (also referred to herein as flex points) ensure the lower tray 110 can expand without breaking. According to an embodiment, the upper tray 100 can also include bi-directional slots 192 similar to those included in the lower tray 10 to allow the upper tray 100 to accommodate a full range of dental arch types as shown in FIG. 20. The upper tray 100 can also include protection walls 156 (shown in FIG. 1) that act in combination with the bi-directional slots to ensure that the upper tray 100 can expand to accommodate various dental arch types.

According to some embodiment, the slots that provide for expansion are only inserted along the bottom surface of the trays. One skilled in the art will recognize that any number of means can be used to ensure the tray does not break when expanded, including use of flexible materials, and/or alternative mechanical means to support stress points created when the trays expand.

FIG. 5 also illustrates positioning tabs 195 designed to force the lower tray 110 open (i.e., increase arch width) as rear molars bite toward the bottom of the lower tray 110. According to an embodiment, the upper tray 100 can also include similarly placed positioning tabs that are designed to force the upper tray 100 open as rear molars bite down on the tray. According to an embodiment, the positioning tabs ensure space is provided for dental material between the outer edges of the upper and/or lower trays and the teeth, and reduces the likelihood the top and bottom edges of the trays come into contact with the user's the gums.

According to an embodiment, the positioning tabs 195, located near the posterior edges of the tray, can terminate prior to the bottom of the tray to create dead space to improve dental material retention. Furthermore, the slots in the positioning tabs can assist with alignment when impression material is reinserted into a tray. Upper tray 100 can also include positioning tabs similar to those included on the lower tray 110. For example, FIG. 20 illustrates a top view of the upper tray 100 and upper tongue portion 155 of the appliance where the positioning tabs 197 can be seen. According to an embodiment, arch expansion controller tabs 215 on the upper tray 100 (visible in FIG. 6) can provide for symmetrical upper tray and lower tray expansion.

FIG. 5 also illustrates another aspect of the lower tray 110 that allows the position of the lower tray 110 to be adjusted in relation to the upper tray 100. The tongue of the lower tray 110 includes a series of holes 240 along the left and right sides of the tongue. The holes 240 can be used in positioning the upper tray 100 relative to the lower tray 110. According to an embodiment, the holes are spaces such that an adjustment precision of 1 mm is provided. This refined degree of advancement is accomplished without use of screws and is typically available only in custom appliances. In one embodiment, a range of 26 mm is used to accommodate extreme retrognathic neutral positions (i.e., overbite of 7 mm) as well as extreme prognathic (i.e., 18 mm) maximum protrusions while minimizing the length of the adjustment tongue for patients who sleep prone. One skilled in the art will recognize that the length of the adjustment tongue can be further reduced by limiting the wide range of occlusal relationships or making different sizes to accommodate extreme retrognathic and prognathic conditions.

According to an embodiment, the material used to retain the appliance to the teeth should reduce the risk of dental morbidity (especially when fitted in the absence of a dental history or oral evaluation), accommodate periodontal compromised or missing teeth, and be sufficiently malleable to accommodate overjet. The retention material allows the appliance to be removably affixed to the teeth to maintaining a position of a patient's upper jaw relative to a position of the patient's lower jaw.

Figure 21:
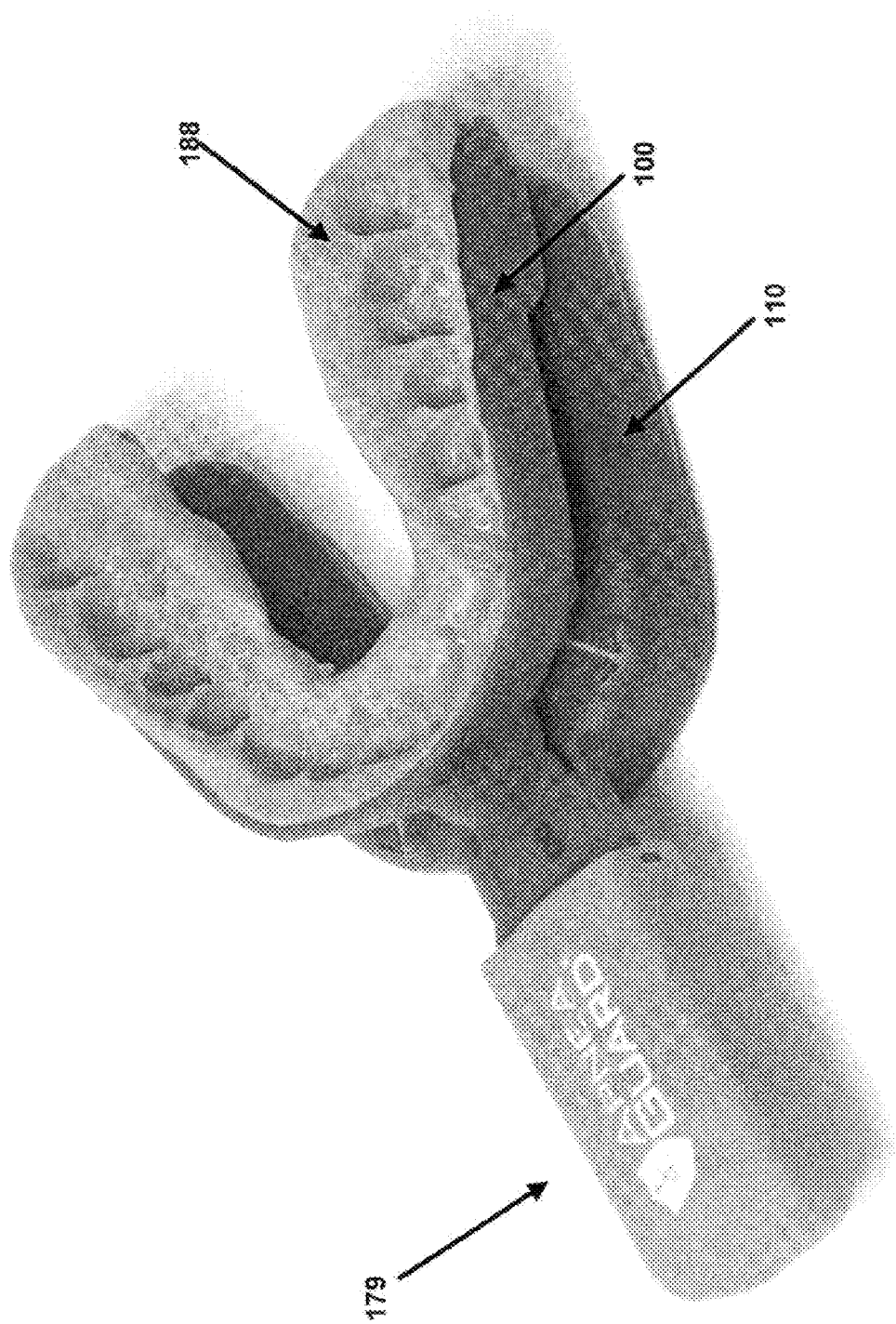
FIG. 21 illustrates a perspective view of the appliance with the silicon cover in place and the retention material in the upper tray according to an embodiment.
Figure 23:
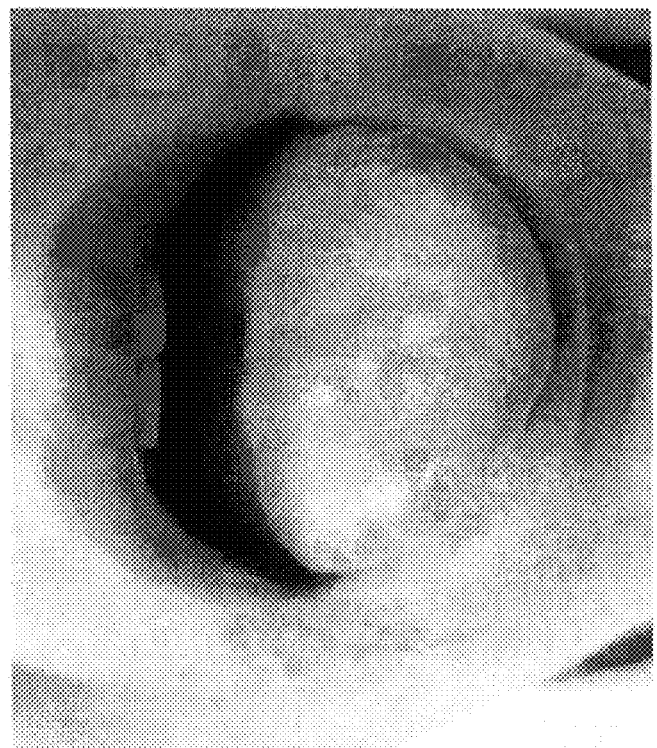
FIG. 23 is an image of a human tongue illustrating a tongue that has a non-scalloped edge.
Figure 22:
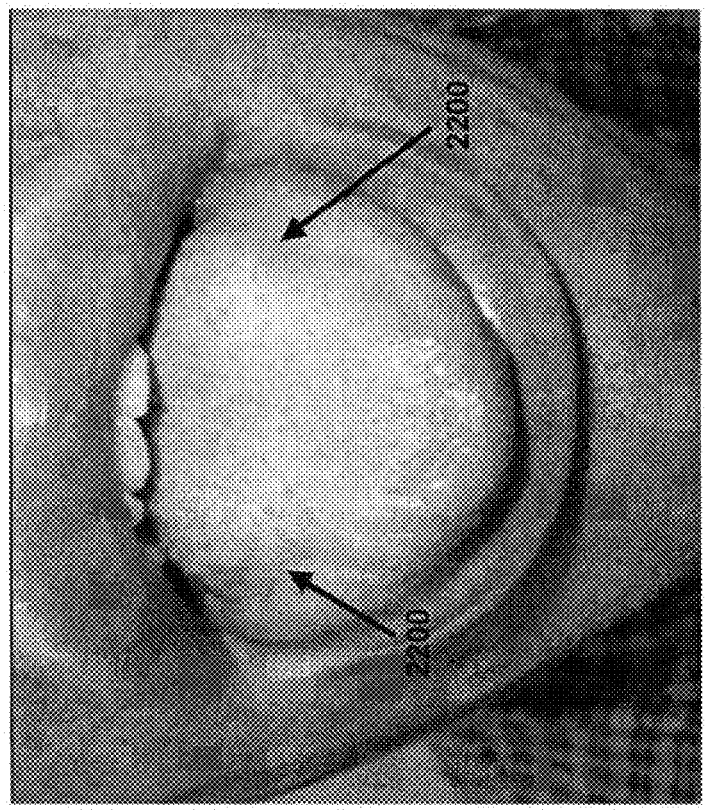
FIG. 22 is an image of a human tongue illustrating a tongue having a scalloped edge.

In a preferred embodiment, the retention material can comprise vinyl plus silicone chemical mixture, because these materials can be readily compounded and immediately used. In one embodiment, the amount of retention material (i.e., catalyst and base) used to prepare a tray can be carefully controlled to minimize extruding of excess material. As described above, extrusion of excess retention material could cause the upper tray 100 to be inadvertently bonded to the lower tray 110. Control of the optimum volume of retention material can be achieved by multiple means, including, but not limited to, the use of a custom sized scoop for measuring portions of the catalyst and/or the base. In another embodiment, individually packaged, pre-measured portions of catalyst and base can be provided for the upper and/or lower tray(s). One skilled in the art will recognize that the volume of retention material to be controlled is dependent on the height of the tray walls and other factors related to the dimensions of the tray and the type of retention material to be used. In alternative embodiments, thermoplastic materials (which requires boiling water to fit), laminate, or acrylic materials can be incorporated into the trays described in FIG. 1 through 6 to retain the teeth. FIG. 21 illustrates an embodiment of the oral appliance that includes retention material 188 in the upper tray 100 that has been used to capture an impression of the upper dental arch of a patient. The lower tray 110 also includes retention material that has been used to capture an impression of the lower dental arch, but the retention material is obscured in the figure.

According to an embodiment, texture, tray features, such as holes or slots in the vertical walls of the upper and lower trays, felt-like material, or a combination thereof can be applied to the inside of the trays to bond the retention material to the tray(s). In a preferred embodiment, bonding can be achieved in a manner that allows the retention material to be removed intact, and allow the trays to be reused with new retention material. The capability of removing and replacing the retention material is beneficial if the initial fitting of the retention material needs to be repeated to improve the quality of the fit. In some embodiments, the intact retention material can be removed from the upper tray 100 and/or lower tray 110 and can be reinserted into a different tray. As a result, the efficacy of the treatment can be assesses over a range of VDO settings while controlling the protrusive dimension. Furthermore, in embodiments where the retention material can be removed intact, the retention material can be removed and used for bite registration for a custom appliance. Meanwhile, the upper tray 100 and/or lower tray 110 can be refitted with new retention material that can be used until the custom appliance is received. Thus, the patient can continue to wear the appliance while waiting for the custom appliance to be fabricated.

In some embodiments, the upper tray 100 and/or the lower tray 110 can include retention posts that can be used to secure retention material in the tray. For example, in the embodiment illustrated in FIG. 5, the lower tray 110 can include retention posts 200 that extend from the base of the lower tray 110 to secure the retention material. FIG. 20 illustrates an embodiment of the upper tray 100 that includes retention posts 202 that extend from the base of the upper tray 100 that can be used to secure the retention material according to an embodiment. In some embodiments, the retention post height can be adjusted to control VDO independent of the neck height. In some embodiments, the VDO can be adjusted by adjusting the height of the retention posts and the neck height. The retention posts can also provide a means to align the retention material when it is inserted into a different tray. Texturing of the tray walls and retention posts, and the shape of the retention posts are controlled to optimize adherence and removal of the retention material to the plastic tray(s).

Figure 6:
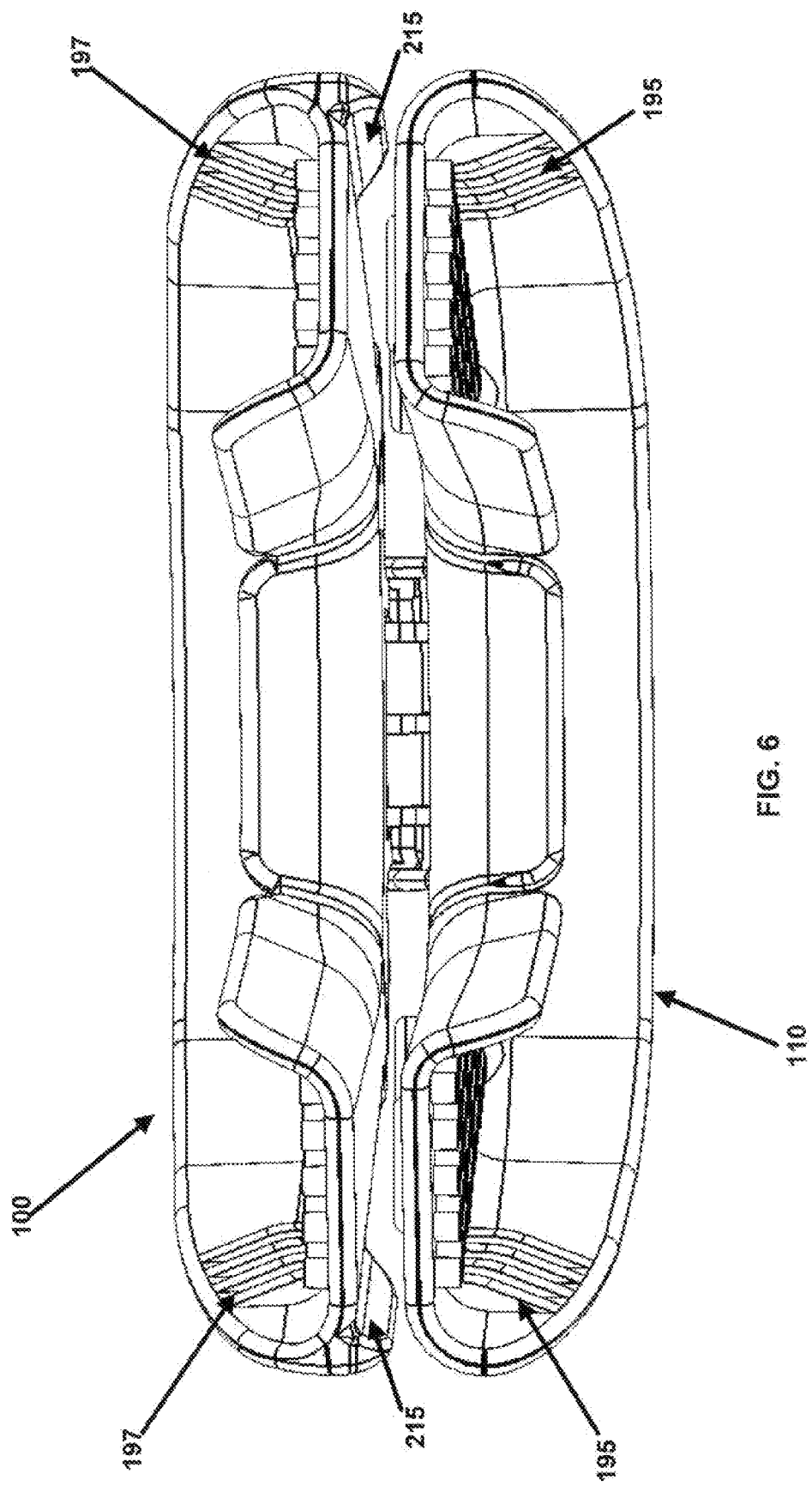
FIG. 6 is an end view of the appliance illustrated in FIGS. 1-5 where both the upper tray and the lower tray are displayed according to an embodiment.

In a preferred embodiment, tray dimensions can be minimized to optimize comfort while simultaneously providing sufficient surface area to retain to the teeth. FIG. 6 illustrates an embodiment of the appliance illustrated in FIGS. 1-5 where both the upper tray 100 and the lower tray 110 are displayed according to an embodiment. The positioning tabs 197 on the upper tray 100 and the positioning tabs 195 on the lower tray 110 can be seen in the view illustrated in FIG. 6 as can the arch expansion controller tabs 215 found on the upper tray 110.

Figure 7:
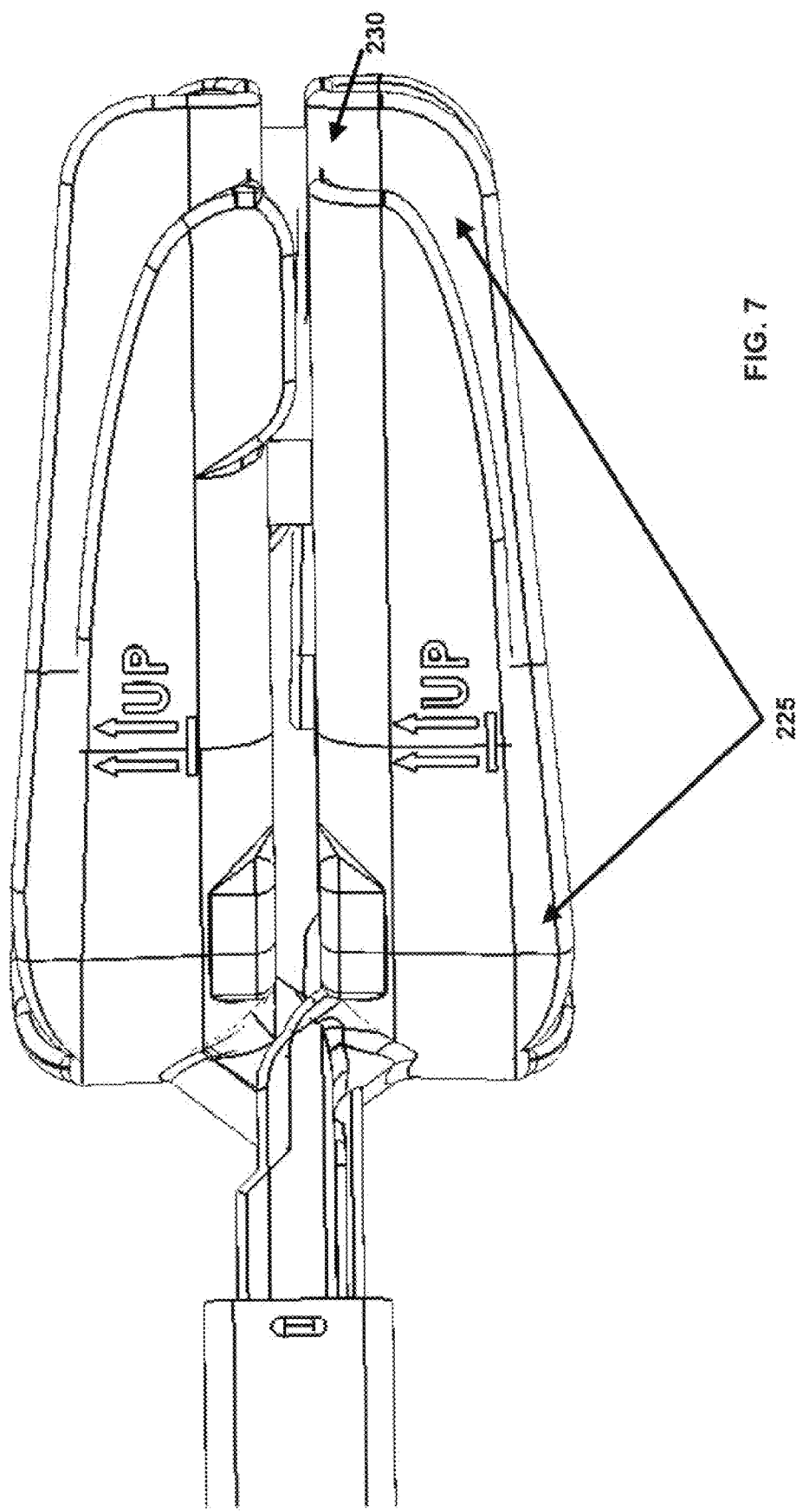
FIG. 7 illustrates an embodiment of the appliance illustrated in FIGS. 1-6 where the tray height and tray length can be reduced without compromising retention according to an embodiment.
Figure 8:
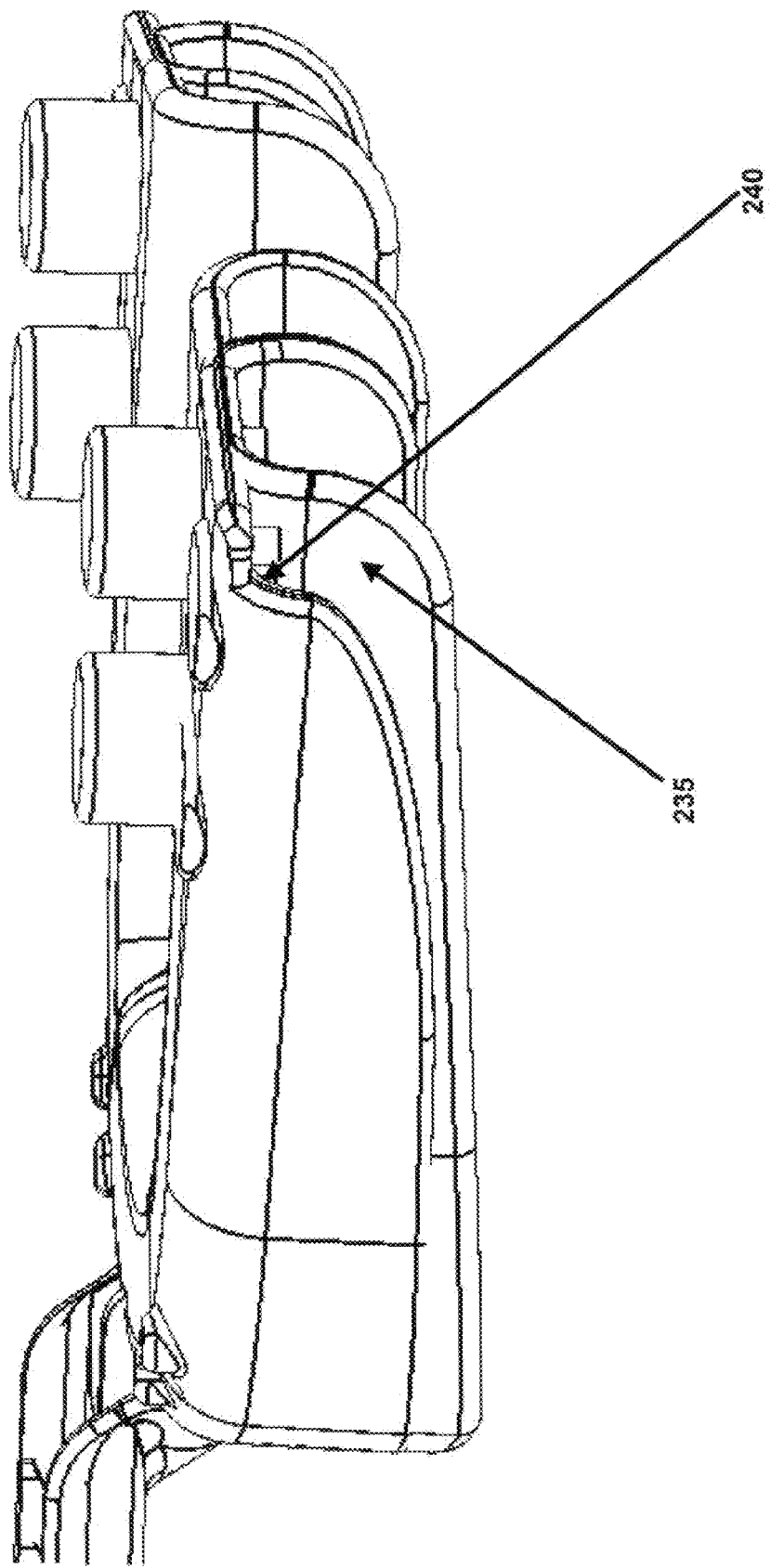
FIG. 8 presents alternative means for decreasing tray length to avoid discomfort according to an embodiment.

FIG. 6 shows the difference in height between the exterior and interior walls of the upper tray 100 and lower tray 110 that increases volume in the oral cavity for the tongue to advance according to an embodiment. In the embodiment illustrated in FIG. 6, the interior walls of the upper tray 100 and lower tray 110 are contoured to encourage the tongue to advance and rest in the space between the upper tray 100 and lower tray 110 provided by the VDO. According to an embodiment, the exterior tray height can be optimized to reduce the likelihood the tray walls rub against the gums when the teeth are not centered in the tray. According to an embodiment, the tray length can also be optimized to avoid discomfort attributed to the outer wall rubbing against peripheral oral structures when the jaw is advanced. FIG. 7 illustrates an embodiment of the appliance illustrated in FIGS. 1-6 where the tray height 225 and tray length 230 can be reduced (as compared to a conventional custom appliance dimensions) without compromising retention according to an embodiment. In one embodiment, the tray length can be reduced to extend to approximately 50% of the second molar without compromising retention. FIG. 8 illustrates an embodiment that is configured to reduce the likelihood of the lower tray 110 rubbing against the fossa by reducing the lateral exterior tray corners 240 in combination with a reduced tray height 235 according to an embodiment. According to an embodiment, similar modifications can be made to the upper tray 100 to reduce the likelihood of the upper tray 100 rubbing against the fossa.

Figure 9:
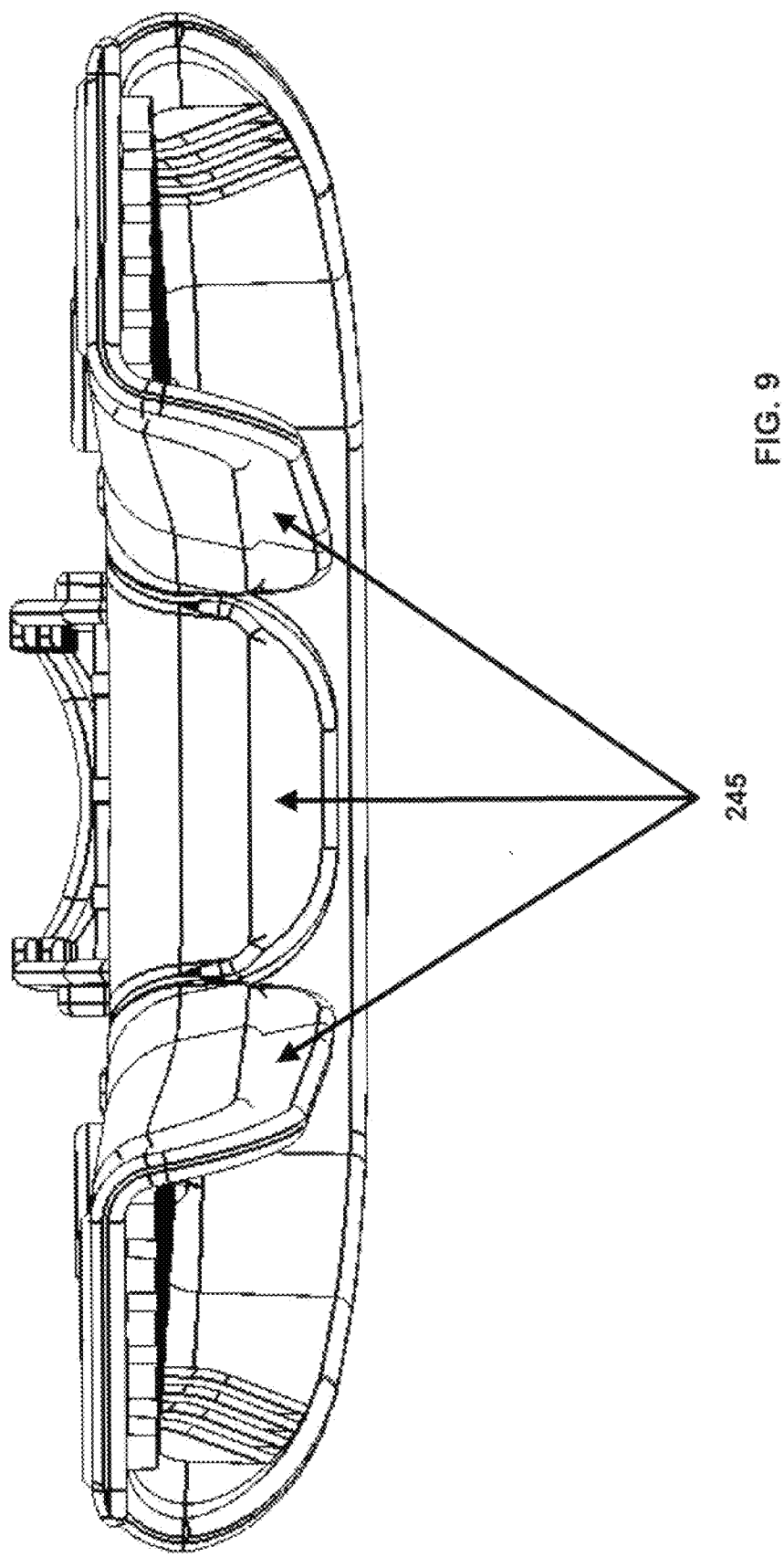
FIG. 9 illustrates an embodiment of the lower tray that demonstrates how the length of the interior walls of the lower tray can be reduced to provide more room for the tongue to advance according to an embodiment.

FIG. 9 illustrates an embodiment of the lower tray 110 that demonstrates how the length of the interior walls 245 of the lower tray 110 can be reduced to provide more room for the tongue to advance according to an embodiment. As mentioned previously, the optimal volume of retention material is dependent on the tray dimensions and the dispensed amount should be adjusted based on dimensions to reduce overflow of material that can rub against the cheeks and gums and cause irritation, induce salivation, or reduce volume in the oral cavity for the tongue to advance. According to an embodiment, the inner walls of the upper tray 100 of the appliance can also be reduced to provide more room for the tongue to advance.

FIG. 10 is an illustration the appliance illustrated in FIGS. 1-9 that illustrates how the upper tray 100 can be aligned with the lower tray 110 according to an embodiment. FIG. 10 illustrates locking holes 250 on the upper tongue 150 of upper tray 100 which align with corresponding locking holes 240 in the lower tongue 155 of the lower tray 100. The appliance can be set to a particular protrusion setting by aligning the holes 250 on the upper tongue 150 of the upper tray 110 with the holes 255 on the lower tongue 155 of the lower tray 110. Values 260 along the lower tongue 155 of the lower tray 110 correspond to the locking holes 240. In the embodiment illustrated in FIG. 8, the value aligned with the edge of the upper tongue 150 of the upper tray 100 indicates the current protrusion setting for the appliance. According to an embodiment, the values 260 represent the current protrusion setting in millimeters. For example, in the embodiment of FIG. 8, the current protrusion setting is "8" indicating that the current protrusion setting is 8 millimeters. Thus, measurements required to establish the initial setting (i.e., based on neutral and maximum advancement) or identify a protrusion level associated with an efficacious outcome can be derived without the need for a secondary tool (e.g., George gauge). Retaining members 290 on the lower tray ensure the upper tray 100 cannot become detached from the lower tray 110 when the two trays are not locked.

FIG. 11 provides a table that can be used to look up a recommended advancement setting for the appliance according to an embodiment. The table illustrated in FIG. 11 provides data for determining a 70% protrusion setting based on any combination of neutral and maximum settings obtained with the appliance. One skilled in the art will recognize that lookup tables for determining other recommended advancements settings based on different percentages can also be provided.

The embodiment of the appliance illustrated in FIG. 10 includes a region 280 on the upper tray 100 where the neutral, maximum and recommended (e.g., 70%) advancement settings can be written thr quick reference by medical staff.

Figure 12:
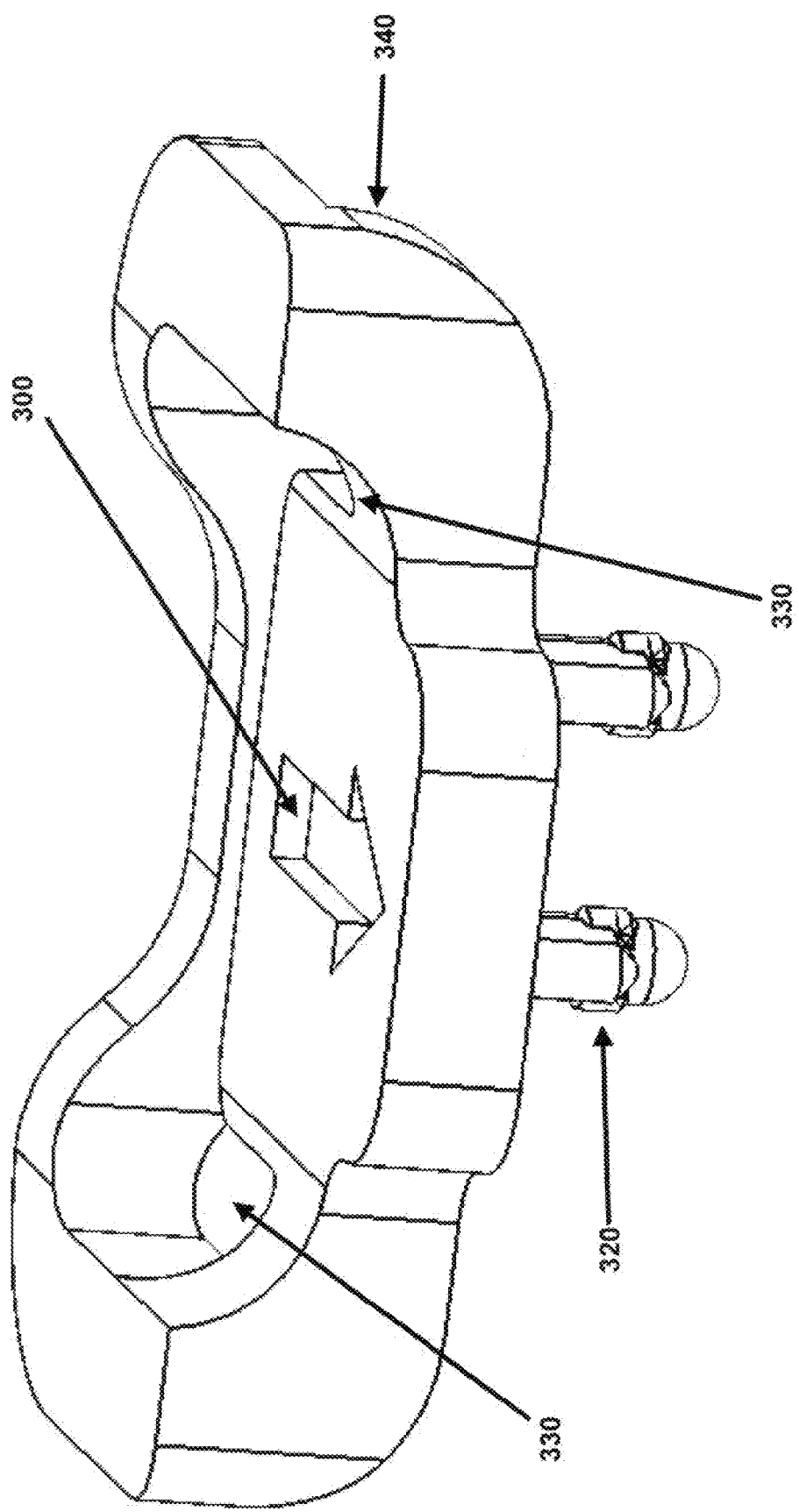
FIG. 12 illustrates the features of the upper and lower tray locking mechanism according to an embodiment.

FIG. 12 illustrates an example of a locking mechanism that can be used to lock the upper and lower trays into position according to an embodiment. The locking mechanism can be used with the embodiments of the appliance illustrated in FIGS. 1-10 and described above. The locking mechanism can be used to fix the position of the upper tray 100 relative to the lower tray 110 once a protrusion setting has been selected. The locking mechanism prevents the upper tongue 150 of the upper tray 100 from sliding along the retaining members 290 relative to the lower tongue 155 of the lower tray 110 while the retaining members keep the two tongues from separating. The locking mechanism includes a pair of locking posts 320 that can be inserted into holes 250 of the upper tongue portion 150 of the upper tray 100 and into the corresponding holes 240 of the lower tongue portion 155 of the lower tray 110 aligned with the holes 250. According to an embodiment, the locking posts can include features on the distal end of the posts that protrude beyond the holes in the lower tray to provide some resistance during insertion and removal of the locking mechanism. In one embodiment the posts provide a snap fit to the holes. In some embodiments, a different number of locking posts can be used to prevent the upper tongue 150 of the upper tray 100 from sliding along the retaining members 290 relative to the lower tongue 155 of the lower tray 110. For example, in an embodiment, a single locking post can be used. In other embodiments, other types of locking mechanisms can be employed to prevent the upper tongue 150 of the upper tray 100 from sliding along the retaining members 290 relative to the lower tongue 155 of the lower tray 110.

In the embodiment illustrated in FIG. 12, the locking mechanism includes an arrow-shaped indicator 300 that points in the direction of the protrusion setting at which the appliance is locked. In the embodiment illustrated in FIG. 12, when the arrow-shaped indicator is pointing left, the locking mechanism is securing even units (millimeters) of protrusion, and when the arrow-shaped indicator is pointing right, the locking mechanism is securing odd units (millimeters) of protrusion. One skilled in the art will recognize that other types of indicators can be used to indicate the current protrusion setting of the appliance. Furthermore, one skilled in the art will recognize that other types of locking mechanisms can be used to lock the relative position of the upper and lower trays of the appliance.

Figure 13:
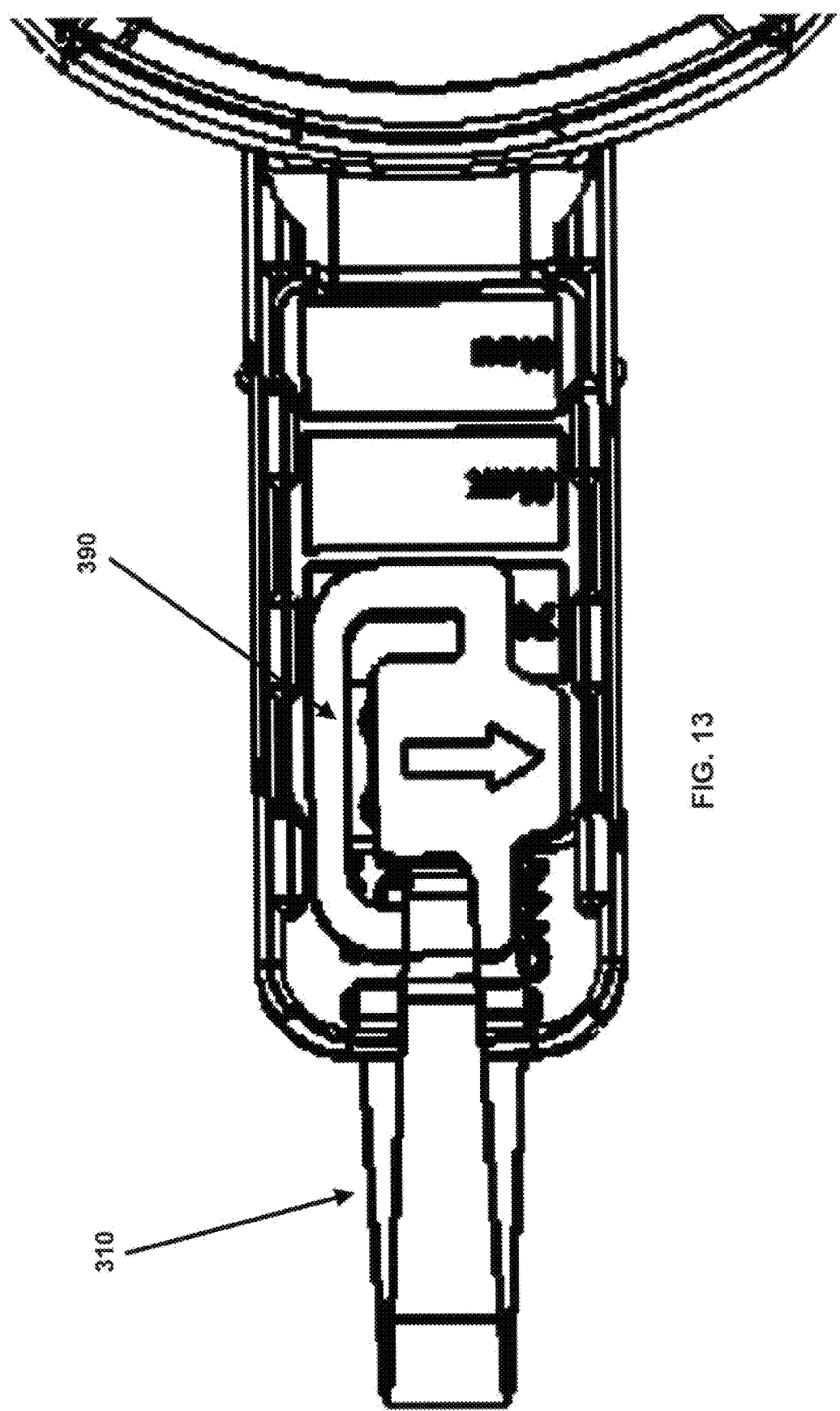
FIG. 13 illustrates an alternative embodiment of the locking mechanism illustrated in FIG. 12 that can also be used with the various embodiments of the appliance illustrated in FIGS. 1-10 according to an embodiment.

According to an embodiment, the locking mechanism can include an opening or openings that can be used to tether the locking mechanism to the appliance. The tether allows the locking mechanism to be connected to either the upper tray, the lower tray, or both even when the locking mechanism is being used in a locking position to maintain the position of the upper tray and lower tray relative to one another. For example, the embodiment of the locking mechanism illustrated in FIG. 12 includes two openings 330 through which a tether can be inserted. In the embodiment illustrated in FIG. 12, the lower tongue portion 155 of the lower tray 110 includes a slot 270 through which a tether can be inserted. FIG. 13, described below, illustrates an example of one type of tether that can be used to tether the locking mechanism to the appliance according to an embodiment.

In the embodiment illustrated in FIG. 12, the tether loop can be can be insert through one of the openings 330 depending on whether the locking mechanism is being used to secure an odd or even protrusion distance for the appliance. In the embodiment illustrated in FIG. 12, the locking mechanism also includes contoured edges 340 at each end of the locking mechanism. The contoured edges 340 provide tab-like feature on each end of the device that provide points for gripping the device and can facilitate removal of the locking mechanism from the appliance when adjustment of the protrusion setting of the appliance is required.

FIG. 13 illustrates an alternative embodiment of the locking mechanism illustrated in FIG. 12 that can also be used with the various embodiments of the appliance illustrated in FIGS. 1-10 above according to an embodiment. FIG. 13 includes a U-shaped opening 390 that can be used to tether the locking mechanism to the appliance rather than the openings 330 illustrated in the embodiment of FIG. 13.

The locking mechanism can be tethered to the appliance to prevent the locking mechanism from being lost, dropped, or swallowed. If the locking mechanism were not tethered to the appliance, the locking device could be misplaced and the appliance would not be able to be locked into at a preferred protrusion distance in embodiments that use a locking mechanism to maintain the preferred protrusion distance settings for the appliance. Tether 310 can be used to keep the locking mechanism available but out of the way during while performing an initial fitting of the appliance for a patient. In the embodiment illustrated in FIG. 13, the tether 310 is secured to the lower tray 110 by inserting the tether into the slot 270 of tongue 155 of the lower tray 110.

FIG. 14 is a flow diagram of a method that can be used to prepare the appliance illustrated in FIGS. 1-13 for use with a patient according to one embodiment. In the embodiment illustrated in FIG. 14, a retention material is used to make an impression of a patient's dentition. This impression can then be used to create a custom appliance based on the patient's dentition.

Retention material is placed in either the upper tray 100 and/or the lower tray 110 to make an impression of the patient's dentition to customize the appliance to the patient who will be using the appliance (step 1400). According to an embodiment, various types of retention materials can be used to make the impression of the patient's dentition. For example, sodium alginate, polyether, silicone, or other nontoxic materials can be used to make the impression. In some embodiments, the retention material may require a catalyst be mixed with a base to initiate a reaction that causes the retention material to set. The catalyst and base can be mixed and then the mixture placed in the tray or trays to be fitted. In some embodiments, an impression of both the upper and the lower arches of the patient's teeth can be captured at the same time.

The tray with the retention materials is inserted into the patient's mouth and the patient is instructed to bite down on the tray or trays containing the retention material (step 1410). The patient maintains the bite on tray containing the retention material while the retention material sets. In embodiments where an impression using only one of the trays was captured in steps 400 and 410, these steps will be repeated for the second tray to capture an impression of the arch of the patient's teach for which an impression has not yet been made.

According to an embodiment, once the retention material hardens, the retention material can be removed and excess material can be cut away to improve the fit and comfort of the appliance. The retention material can then be reinserted into the tray. This process can be repeated for both trays to improve the fit and comfort of the trays in the patient's mouth.

Once an impression has been made for both the upper and lower trays, a protrusion setting in the neutral position can be determined while the patient has the upper and lower trays in place in the mouth (step 1420). The neutral bite position is the position where the patient's upper and lower jaws naturally rest in a closed position. According to an embodiment, the neutral position can be marked directly on the appliance by medical staff. For example, as described above with respect to FIG. 10, the upper tray 100 can include a region 280 where the medical staff can record advancement settings directly on the appliance where the settings can be quickly referred to by medical staff. For example, in an embodiment, the region 280 can include areas where neutral, maximum and recommended (e.g., 70%) advancement settings can be recorded directly on the appliance. According to an embodiment, the advancement settings can be measured in millimeters. As described above, the value 260 along the tongue 155 of the lower tray 110 correspond to the holes 255 and can be used to indicate the current protrusion setting of the appliance. In some embodiments, the values 260 can be used to indicate the protrusion setting in millimeters. One skilled in the art will recognize that other measurement increments can be used.

A protrusion setting for the maximum position can then be determined (step 1430). According to an embodiment, the protrusion setting for the maximum position can be obtained by instructing the patient to extend their lower jaw forward as far as possible without assistance and measuring the position of the jaw at that point. According to an embodiment, the maximum position setting can be recorded directly on region 280 of the upper tray 100 for quick reference by medical staff.

A recommended advancement setting can then be determined (step 1440). According to an embodiment, the recommended advancement setting can then be determined by subtracting the neutral setting from the maximum setting and multiplying the difference by an advancement percentage. According to an embodiment, the result of calculation can then be added to the neutral setting to determine the recommended advancement setting. According to a preferred embodiment, an advancement percentage of 70% can be used to determine the recommended advancement setting. However, alternative advancement settings are also be used (e.g., 60%, 80%, or other percentages).

According to an embodiment, a lookup table can be used to facilitate rapid determination of the recommended advancement setting. FIG. 11 provides an example of such a lookup table that can be used to look up a 70% recommended advancement setting based on neutral and maximum position settings determined while the patient is wearing the appliance. Neutral position settings are listed in millimeters horizontally and maximum position settings are listing in millimeters. The recommended advancement setting can be found by identifying value where the column that corresponds to the neutral position setting and the row that corresponds to the maximum position setting intersect. According to an embodiment, the recommended position setting can be recorded directly on region 280 of the upper tray 100 for quick reference by medical staff.

According to another embodiment, the recommended advancement setting can be determined using an incremental process. In this incremental process, the protrusion setting for the appliance can be set to an initial value by medical staff and the patient can then be instructed to increase the protrusion on the appliance by a predetermined increment at predetermined intervals until an optimal advancement setting is achieved. In an embodiment, the optimal advancement setting can be determined by monitoring daytime sleepiness in the patient, snoring levels, using sleep study measures, or a combination thereof in an example embodiment, the initial advancement percentage can be set to 60% and the patient can be instructed to incrementally increase the protrusion setting by 1 mm per week. In an alternate embodiment, the initial advancement setting for the appliance can be set to a higher advancement setting (e.g. 80%) and to incrementally decrease the protrusion setting by 1 mm per week. One skilled in the art will recognize that other initial advancement percentages can be used, that other incremental increases or decreases of the protrusion settings and can be used, and that the interval over which the increases or decreases are monitored for efficacy can also be shorter or longer periods of time.

Once the recommended advancement setting has been determined, the position of the upper tray 100 can be adjusted relative to the lower tray 110 such that the protrusion setting for the appliance is equal to the recommended protrusion setting (step 1450). According to an embodiment, the positions of the trays can then be locked into place using a locking mechanism, such as those illustrated in FIGS. 12 and 13, to keep the trays in the recommended position while in use by the patient. As described above, a locking mechanism can be inserted through one or more holes in the upper tongue portion 150 of the upper tray 110 and one or more holes in the tongue 155 of the lower tray.

According to an embodiment, once the upper and lower trays are secured in step 440, a silicone cover can be placed over the end of the tongue of the appliance, the tether 310, locking mechanisms, providing a sanitary handle for removal of the appliance by a third party (e.g., the medical staff when the appliance is being worn in a hospital setting) (step 1460).

Unique aspects of systems and methods disclosed herein can be appreciated by non-dental care givers. All of the components required for use of the appliance can be included in a single kit that can be fitted in minutes by a staff member with limited technical expertise. The formulary of the retention material is matched to the retention features so that the retention materials can be removed and the tray reused if the appliance was not initially fitted properly. The appliance can also be safely on patients who have not undergone a dental examination.

Ready access to remove and reset the locking mechanism has multiple beneficial applications. According to an embodiment, the appliance can be advanced to maximum protrusion in a surgical recovery room so that staff can avoid manual post-anesthesia "chinning." In one embodiment, the appliance can be configured such that the anterior VDO is sufficient to allow for insertion of standard suction tips for management of secretions. While this degree of vertical dimension may be uncomfortable for continued use during sleep, one skilled in the art will recognize that this particular configuration of the invention can be dedicated to post-surgical recovery.

After recovery from anesthesia, the protrusive jaw setting can be adjusted to the recommended optimal setting while the patient is on hospital floor or after discharge while the patient is on narcotic pain medication. Importantly, there are no critical parts that can be misplaced when the patient is transferred between areas in the hospital or wearing the appliance in the home, because the components of the device remain connected and/or tethered together.

According to an embodiment, the neutral, maximum and optimal measurements are available for quick reference if the appliance should need to be adjusted by medical staff during recovery. As importantly, in patients who are not responding to the predicted optimal setting, the neutral and maximum protrusion settings can be taken and compared to the previous measures to confirm the accuracy of the initial measurements. Because protrusion is adjusted outside the mouth, the invention can be adjusted by medical staff while the appliance is inserted in the patient's mouth. For example, a technician could adjust the protrusion settings of the appliance while a patient is undergoing an attended sleep study.

FIG. 15 is a flow diagram of a process for utilizing the appliance disclosed in the FIGS. 1-13 in sleep centers that diagnose and/or treat sleep-related disorders according to an embodiment. The method disclosed in FIG. 15 can be used to determine the parameters for one or more custom appliances that fit the needs of a patient using an adjustable temporary appliance, such as those disclosed in FIGS. 1-13. The custom appliances can still be fine-tuned to provide the efficacious treatment for OSA for a patient. The method of FIG. 15 also eliminates the dependence on a dentist to develop a set of optimal settings for a custom appliance for a patient based on trial and error.

According to an embodiment, a temporary appliance can be fitted by non-dental staff at a sleep center (step 1500) who can determine an optimal protrusion setting and VDO for a patient before recommending that a custom appliance be created for the patient. In an embodiment, the appliance can be fitted using the techniques described in steps 1400 and 1410 of the method illustrated in FIG. 14. According to an embodiment, the sleep center staff can refer to a predictive model to determine an initial protrusion and VDO settings for the patient. For example, the staff can refer to the data such as that illustrated in FIGS. 17A and 17B (described below) that plots anticipated changes in untreated apnea/hypopnea index (AHI) for mail and female patients based on various VDO settings. Other similar models derived from patient data can be used to determine initial VDO and/or protrusion settings to be used with a patient.

Figure 17A:
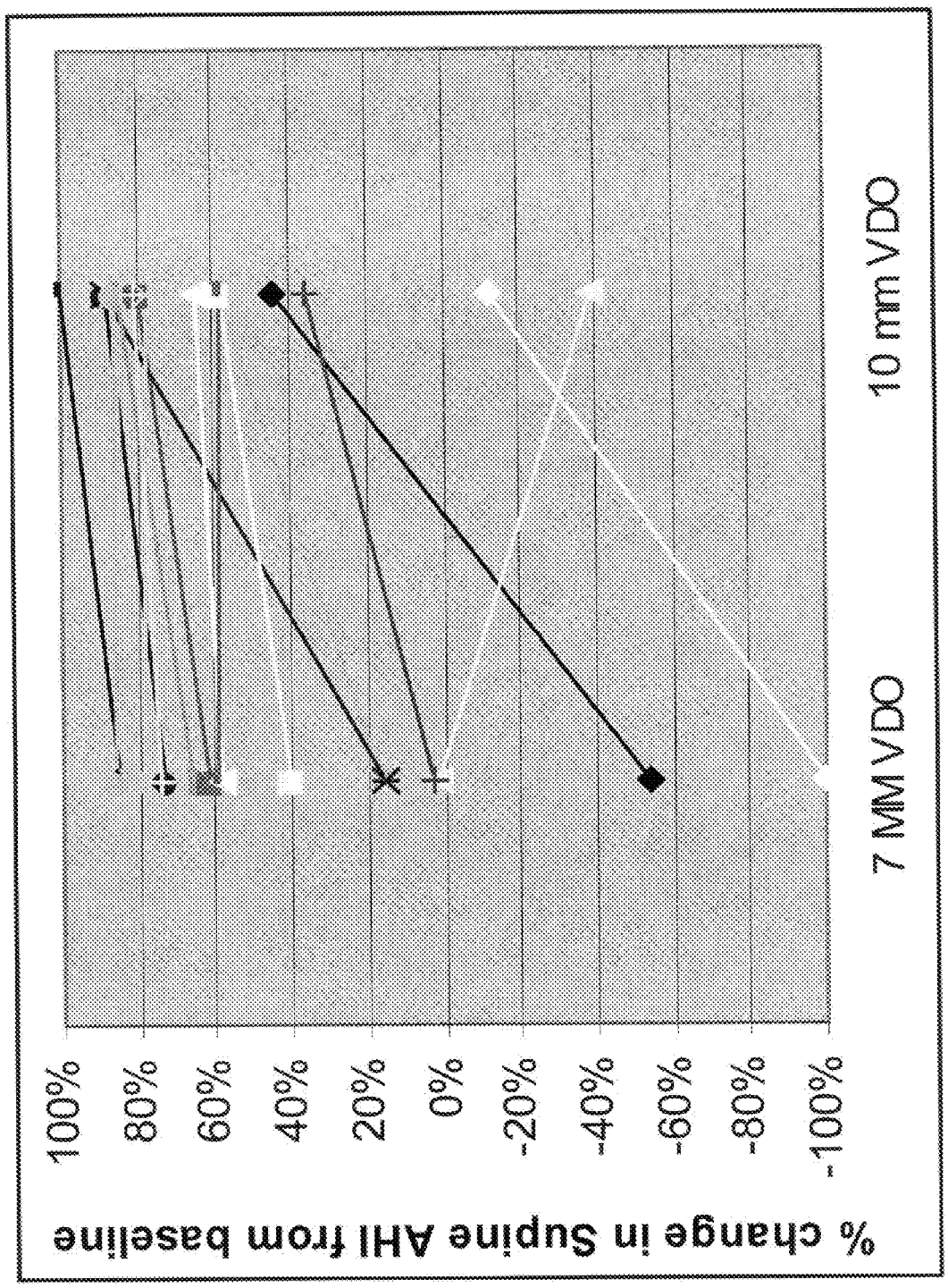
FIGS. 17A and 17B are two histograms showing the impact of VDO on treatment outcomes when male and female patients are sleeping supine according to an embodiment.
Figure 17B:
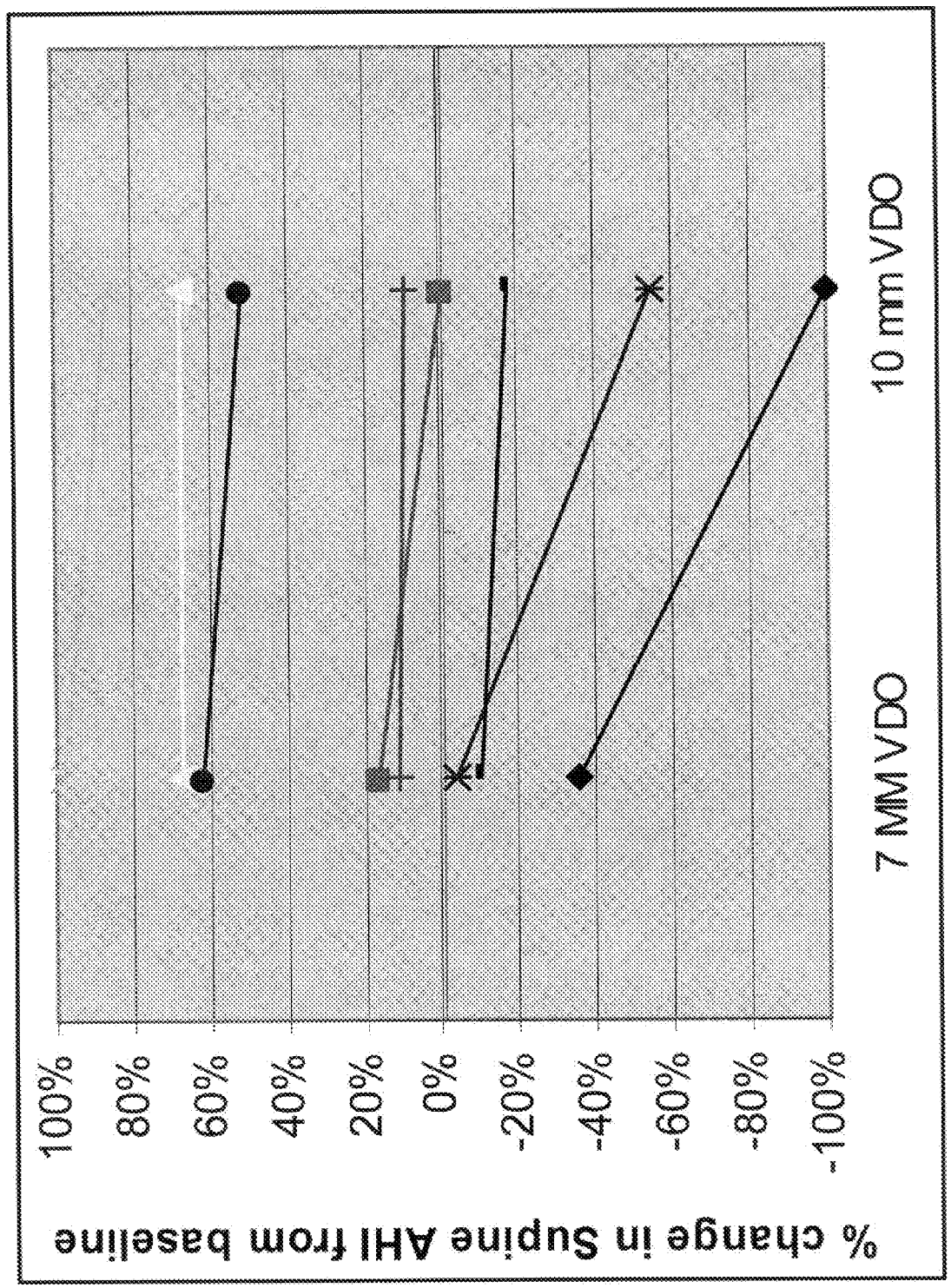

The staff can then determine a set of adjusted settings for the temporary appliance for the patient (step 1510). In an embodiment, the staff can determine a set of adjusted settings for the patient using the technique described in steps 1420, 1430, and 1440 of the method illustrated in FIG. 14. The selection of VDO is determined, in part, by gender. FIGS. 17A and 17B show males have better outcomes with increased VDO. Patients who sleep predominantly (e.g., more than 30% of the night) on their back are also candidates for increased VDO. According to an embodiment, an optimal VDO for a patient can be determined based on gender, supine sleep time, size of the patient's tongue, protrusion ranges (neutral and maximum) at different VDO settings, or a combination thereof. According to an embodiment, an optimal VDO for a patient can also be determined at least in part on the ability for the patient to maintain a good lip seal while wearing the appliance at that VDO setting to reduce the likelihood of mouth breathing and loud snoring.

According to an embodiment, an optimal VDO for a patient can also be determined at least in part on the apnea/hypopnea indexes (AHI) for the supine and/or non-supine positions or the ratio of supine vs. non-supine AHI. The AHI is an index of severity that can be used to quantify the overall sleep apnea of a patient. The AHI takes into account sleep disruptions and desaturations experienced by the patient. The AHI can be calculated by dividing the number of apneas and hypopneas experienced by a patient divided by the number of hours of sleep for which the patient was monitored. AHI values are typically categorized into three categories: mild, moderate, and severe. An AHI of 5-1.5 events (sleep disruptions) would typically be classified as mild, an AHI of 15-30 events would typically be classified as moderate, and an AHI above 30 events would typically be classified as severe. According to some embodiments, the apneas must last for 10 seconds or more and be associated with a decrease in oxygenation of the blood. The AHI can be can be used to classify the severity of the OSA being experienced by the patient.

FIGS. 17A and 17B present two histograms showing the impact of vertical dimension of occlusion (VDO) on treatment outcomes when male and female patients are sleeping supine according to an embodiment. FIG. 17A illustrates that males have improved outcomes when the VDO is 10 mm and FIG. 17B illustrates that females had better results when the VDO is 7 mm. Males and females with neck sizes greater than 17.5 and 15.5 inches respectively had better results with lower VDO settings. These results support the use of targeted appliance settings for males and females and/or those with identifying characteristics as demonstrated by way of example in Table 2 of FIG. 19. For example, according to the embodiment illustrated in FIG. 19, a male patient having a normal (non-scalloped) tongue that sleeps supine less than 40% of the night would benefit from an appliance that has a medium VDO (e.g., 6.5 mm), while a male patient that sleeps supine less than 40% of the night but has a scalloped tongue would benefit from an appliance that has a high VDO setting. The information included in Table 2 of FIG. 19 can be used when selecting an appropriate appliance for a patent based on the patient's tongue size and sleeping patterns.

Once the temporary appliance has been fitted, a sleep study of the patient can be conducted to determine the efficacy of the protrusion settings and VDO of the temporary appliance (step 1520), and an assessment of the efficacy of the treatment using the oral appliance can be made (step 1525). According to an embodiment, the assessment can be made during an attended sleep study or can be collected in a sleep study conducted in the patient's home using a portable recording device, such as the Data Acquisition Unit disclosed in the U.S. patent application Ser. No. 12/726,084, entitled "System for the Assessment of Sleep Quality in Adults and Children," filed on Mar. 17, 2010, which is incorporated herein by references as if it were set forth in full. According to some embodiments, technicians can adjust the protrusion settings and/or the VDO of the appliance during the course of an attended sleep study to optimize the efficacy of the appliance in treating the patient's OSA.

The sleep center staff can then determine final VDO and protrusion settings based on the results of the sleep study conducted in step 1520 (step 1530). According to some embodiments, adjustments can be made to the VDO and protrusion settings of the appliance and an additional sleep study steps) 1510 can be conducted to fine tune the settings for the temporary appliance. According to an embodiment, the final VDO settings for the appliance can also be determined at least in part on the apnea/hypopnea indexes (AHI) for the supine and/or non-supine positions or the ratio of supine vs. non-supine AHI. In an embodiment, the AHI data can be based on the sleep study data collected for the patient while the patient was wearing the temporary appliance.

Once a set of final settings has been determined, the sleep center staff can request that a custom appliance be fabricated for the patient based on the final settings of the temporary appliance (step 1540). According to an embodiment, the impressions of the patient's dentition that were created using retention material as well as the final protrusion settings and/or VDO settings can be provided to the dental laboratory for fabrication of a custom appliance for the patient. According to an embodiment, the custom appliance does not include an upper tongue portion or a lower tongue portion that protrudes from the patient's mouth. Instead, the custom appliance typically includes one or more screws that can be adjusted by the staff to adjust the protrusion settings of the custom appliances if an adjustment is necessary. As a result, the custom appliance cannot be as quickly adjusted by medical staff. However, the measurements obtained by the staff in the previous steps should provide measurements could be used to create a custom appliance that requires only minimal adjustment.

Once the custom appliance has been received from the dental laboratory, the protrusion settings of the custom appliance can be adjusted as required (step 1550) to ensure efficacy. As described above, a typical custom appliance can include screws or other built-in adjustment means that allows the medical staff to fine-tune the protrusion settings of the custom appliance.

FIG. 16 is a flow diagram of a process for utilizing the appliance disclosed in the FIGS. 1-13 in medical delivery model according to an embodiment. The method disclosed in FIG. 16 can be used to determine the parameters for one or more custom appliances that fit the needs of a patient. The custom appliances can still be fine tuned to provide the efficacious treatment for OSA for a patient. Like the method illustrated in FIG. 15, the method illustrated in FIG. 16 also eliminates the dependence on a dentist to develop a set of optimal settings for a custom appliance for a patient based on trial and error.

In the method illustrated in FIG. 16, a screening questionnaire is used to identify patients likely to have undiagnosed OSA. Responses to the questionnaire are received (step 1600) and a predictive determination can be made based on the results of the questionnaire as to whether the patient has OSA (step 1610). According to an embodiment, various questionnaires can be used to assess the likelihood that the patient has OSA, including the Apnea Risk Evaluation System (ARES) Questionnaire, the STOP questionnaire (focusing on snoring, tiredness during daytime, observed apnea, and high blood pressure) or the STOP/BANG (focuses on the same parameters as the STOP questionnaire but adds the parameters of BMI, age, neck circumference, and gender), Berlin Questionnaire, the Adjusted Neck Circumference, and/or other apnea assessment approaches. All of these approaches rely on information predictive of sleep apnea, including but not limited to age, body mass index, neck size, history or frequency of daytime sleepiness, snoring, witnessed apneas, waking up choking and co-morbidities.

The data collected using the questionnaire or questionnaires can be analyzed to determine a predicted pre-test probability of OSA for the patient (step 1610). According to an embodiment, the data collected can be used in a predictive equation which weights the predictive value of each response or simply tallies the number of responses which exceed a pre-determined threshold to identify 'at-risk' individuals. In a preferred embodiment, more sophisticated linear regression analysis can be used to predict the severity of sleep apnea based on questionnaire responses to more accurately identify those most likely to require oral appliance therapy perioperatively.

The patient can then undergo a sleep study and the results from the sleep study obtained (step 1620). According to an embodiment, nocturnal recording can be made of various physiological characteristics of the patient that can signify that the patient is experiencing OSA. For example, in an embodiment, audio recordings of patient snoring can be recorded to assess snoring magnitude and frequency. In an embodiment, positions sensors can be used to determine the position of the patient while sleeping. Other physiologic indicators, such as pulse oximetry or polysomnography can also be used to collect physiologic data about the patient that can be used to determine whether the patient exhibits symptoms of OSA during the sleep study.

Once the sleep study data has been obtained, a prediction as to the likelihood of appliance efficacy can be made for the patient (step 1630). According to an embodiment, a formula based on the untreated apnea/hypopnea index (AHI) can be employed to predict the likelihood of appliance efficacy. As described above, the AHI is an index of severity that can be used to quantify the overall sleep apnea of a patient. The AHI takes into account sleep disruptions and desaturations experienced by the patient. The AHI can be calculated by dividing the number of apneas and hypopneas experienced by a patient divided by the number of hours of sleep for which the patient was monitored.

A prediction as to the appliance therapy's impact on a patient's AHI can be predicted using a model derived from testing the efficacy of treating OSA patients using the appliance. In an embodiment, the following equation can be employed to predict the post-treatment AHI for the patient:

Predicted post-treatment AHI=(Pre-treatment AHI/5)+2 events

In testing, this linear regression approach accurately predicted 66% of 122 cases within ±3 events/hr and 89% within ±6 events/hr. Only 3% of the cases had predicted errors >±10 events/hr. In alternative embodiments questionnaire responses can be used to further refine the prediction of successful treatment outcomes. The data in Table 1 of FIG. 18 identifies both sleep study and questionnaire response data that are highly correlated with post-treatment AHI as a result of oral appliance therapy. Note that there are differences in the predictive variables which are unique to males and females that support the user of separate predictive models for each gender. As can be seen from these predictive models, the appliance therapy can result in significant decrease in the severity of the OSA a patient experiences while wearing the device.

The predicted efficacy of appliance therapy in combination with additional patient history data can be used to identify patients who will likely have perioperative complications as a result of their unique medical conditions (step 1640). For example, in an embodiment, the predicted post-treatment AHI determined in step 1630 can be combined with other information about the patient's medical history and current medical state to predict whether a patient may experience complications related to a surgical procedure before, during, or after the operation. According to an embodiment, the risk of perioperative complications can be predicted using the Apnea Risk Evaluation Systems disclosed in U.S. patent application Ser. No. 11/955,185 filed on Dec. 12, 2007, which is hereby incorporated by reference as if set forth herein in its entirety. According to an embodiment, the predicted efficacy of the appliance therapy on a patient's OSA can also be used to predict the patient's risk using other models for predicting the perioperative risks for the patient. The predictions generated in step 1640 can be used by medical staff to determine an appropriate course of treatment for a patient based on predicted perioperative complications (step 1650).

Various illustrative implementations of the present invention have been described. However, one of ordinary skill in the art will see that additional implementations are also possible and within the scope of the present invention. The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent exemplary embodiments of the invention and are therefore representative of the subject matter which is broadly contemplated by the present invention. It is further understood that the scope of the present invention fully encompasses other embodiments and that the scope of the present invention is accordingly limited by nothing other than the appended claims.

What is claimed is:

1. An oral appliance for treating obstructive sleep apnea or snoring of a patient through maintaining a position of the patient's upper jaw relative to a position of the patient's lower jaw, the appliance comprising:

an upper tray configured to removably affix to a patient's upper teeth;

an upper tongue portion extending outwardly from the upper tray;

a lower tray configured to removably affix to the patient's lower teeth;

a lower tongue portion extending outwardly from the lower tray, wherein the upper tongue portion and the lower tongue portion slidably engage with each other such that one or both of the upper tongue portion and the lower tongue portion can slide in an anterior and posterior direction relative to the patient's mouth when the upper tray is affixed to the patient's upper teeth and the lower tray is affixed to the patient's lower teeth, and wherein the upper tongue portion and the lower tongue portion extend outside of the patient's mouth when the upper tray is affixed to the patient's upper teeth and the lower tray is affixed to the patient's lower teeth;

a plurality of locking holes located on one of the upper tongue portion and the lower tongue portion, and at least one locking hole located on the other of the upper tongue portion and the lower tongue portion; and an adjustment mechanism having at least one locking post configured to extend through at least one of the plurality of locking holes located on the one of the upper tongue portion and the lower tongue portion and through the at least one locking hole located on the other one of the upper tongue portion and the lower tongue portion when the two holes are aligned and thereby fix a position of the upper tray relative to the lower tray.

2. The appliance of claim 1 wherein the adjustment mechanism is removable to allow the position of the upper tray relative to the position of the lower tray to be adjusted to a selected protrusion setting, and wherein the adjustment mechanism can be reengaged with the upper tongue portion and the lower tongue portion to lock the relative positions of the lower and upper trays into place to maintain the appliance at the selected protrusion setting.

3. The appliance of claim 1 wherein the upper tray and the lower tray each include a set of flex points that allow the upper tray and the lower tray to bend to accommodate various sizes of dental arches.

4. The appliance of claim 1 wherein the adjustment mechanism is removable to allow the position of the upper tray relative to the lower tray to be adjusted, and wherein the adjustment mechanism can be replaced to lock the positions of the lower and upper trays into place.

5. The appliance of claim 1 wherein the upper tray comprises retention material molded to fit the upper teeth of the patient and wherein the lower tray comprises retention material molded to fit the lower teeth of the patient.

6. The appliance of claim 5 wherein the upper tray and the lower tray include retention posts to secure the retention material to the upper tray and the lower tray.

7. The appliance of claim 6 wherein the retention material is removable and reusable when inserted into the same or a different tray.

8. The appliance of claim 1 wherein the plurality of locking holes correspond to protrusion settings, and wherein the at least one locking post is configured to be inserted through at least one of the plurality of locking holes that corresponds to a selected protrusion setting.

9. The appliance of claim 1 further comprising a retaining portion, wherein the retaining portion comprises a set of retaining members that allow one of the upper tongue portion and the lower tongue portion to slidably engage with the other of the upper tongue portion and the lower tongue portion.

10. The appliance of claim 1 wherein the adjustment mechanism is attached to at least one of the upper tray or the lower tray even when the adjustment mechanism is not in a locked position.

11. An oral appliance for treating obstructive sleep apnea or snoring of a patient through maintaining a position of the patient's upper jaw relative to a position of the patient's lower jaw, the appliance comprising:

an upper tray configured to removably affix to a patient's upper teeth;

an upper tongue portion extending outwardly from the upper tray;

a lower tray configured to removably affix to the patient's lower teeth;

a lower tongue portion extending outwardly from the lower tray, wherein the upper tongue portion and the lower tongue portion slidably engage with each other such that one or both of the upper tongue portion and the lower tongue portion can slide in an anterior and posterior direction relative to the patient's mouth when the upper tray is affixed to the patient's upper teeth and the lower tray is affixed to the patient's lower teeth;

a plurality of locking holes located on one of the upper tongue portion and the lower tongue portion, and at least one locking hole located on the other of the upper tongue portion and the lower tongue portion;

an adjustment mechanism having at least one locking post configured to extend through at least one of the plurality of locking holes located on the one of the upper tongue portion and the lower tongue portion and through the at least one locking hole located on the other one of the upper tongue portion and the lower tongue portion when the two holes are aligned and thereby fix a position of the upper tray relative to the lower tray; and a retaining portion, wherein the retaining portion comprises a set of retaining members that allow one of the upper tongue portion and the lower tongue portion to slidably engage with the other of the upper tongue portion and the lower tongue portion.

12. A method for creating an oral appliance for treating obstructive sleep apnea (OSA) or snoring, the appliance maintaining a position of a patient's upper jaw relative to a position of the patient's lower jaw to facilitate breathing while the patient is asleep, the appliance including an upper tray configured to removably affix to the patient's upper teeth and a lower tray configured to removably affix to the patient's lower teeth, the method comprising:

inserting the appliance into the patient's mouth, the appliance having retention material in one or both of the upper tray and the lower tray;

waiting for the retention material to form to the patient's teeth while the patient bites down on the retention material;

determining an initial position measurement for an initial position setting with the appliance while the patient maintains an initial position of the upper and lower jaws;

determining a maximum protrusion measurement for a maximum protrusion setting with the appliance while the patient extends the lower jaw as forward as far as possible without assistance;

determining a recommended protrusion setting based on the initial position measurement and the maximum protrusion measurement; and setting an adjustment mechanism on the appliance to fix a position of the upper tray relative to the lower tray at one of a plurality of protrusion settings to maintain the position of the patient's upper and lower jaws at a fixed relative position while the patient is wearing the appliance.

13. The method of claim 12 wherein determining the recommended protrusion setting based on the initial position measurement and the maximum protrusion measurement further comprises:

subtracting the initial position measurement from the maximum protrusion measurement to determine a displacement value; and multiplying the displacement value by an advancement percentage to determine the recommended protrusion setting.

14. The method of claim 13, wherein the advancement percentage is 70%.

15. The method of claim 13, wherein the advancement percentage is set to a predetermined advancement setting, and wherein the patient is instructed to increase protrusion incrementally until the optimal advancement is achieved determined by changes in daytime sleepiness, snoring levels, or sleep study measures.

16. The method of claim 12, wherein inserting the appliance into the patient's mouth and waiting for the retention material to form to the patient's teeth while the patient bites down on the retention material comprises:

inserting a first one of the upper tray and the lower tray into the patient's mouth, the first tray having first retention material;

waiting for the retention material of the first tray to form to the patient's teeth while the patient bites down on the first retention material;

after inserting the first tray, inserting the second one of the upper tray and the lower tray into the patient's mouth, the second tray having second retention material; and waiting for the retention material of the second tray to form to the patient's teeth while the patient bites down on the second retention material.

17. The method of claim 16, further comprising removing the first tray prior to inserting the second tray.

18. The method of claim 12, wherein the initial position is a neutral occlusal position of the upper and lower jaws.

19. An oral appliance for treating obstructive sleep apnea or snoring of a patient through maintaining a position of the patient's upper jaw relative to a position of the patient's lower jaw, the appliance comprising:

an upper tray configured to removably affix to a patient's upper teeth;

an upper tongue portion extending outwardly from the upper tray;

a lower tray configured to removably affix to the patient's lower teeth;

a lower tongue portion extending outwardly from the lower tray, wherein the upper tongue portion and the lower tongue portion are slidably engaged such that they move smoothly in continuous contact with each other in an anterior and posterior direction relative to the patient's mouth when the upper tray is affixed to the patient's upper teeth and the lower tray is affixed to the patient's lower teeth, and wherein the upper tongue portion and the lower tongue portion extend outside of the patient's mouth when the upper tray is affixed to the patient's upper teeth and the lower tray is affixed to the patient's lower teeth;

a plurality of locking holes located on one of the upper tongue portion and the lower tongue portion, and at least one locking hole located on the other of the upper tongue portion and the lower tongue portion; and an adjustment mechanism having at least one locking post configured to extend through at least one of the plurality of locking holes located on the one of the upper tongue portion and the lower tongue portion and through the at least one locking hole located on the other one of the upper tongue portion and the lower tongue portion when the two holes are aligned and thereby fix a position of the upper tray relative to the lower tray.

20. A method for using an oral appliance to maintain a patient's jaws at a fixed relative position, wherein the oral application comprises an upper tray configured to removably affix to the patient's upper teeth and a lower tray configured to removably affix to the patient's lower teeth, the method comprising:

determining an initial position measurement from a protrusion setting of the oral appliance while the patient maintains an initial position of the upper and lower jaws;

determining a maximum protrusion measurement from a protrusion setting of the oral appliance while the patient extends the lower jaw forward as far as possible without assistance;

subtracting the initial position measurement from the maximum protrusion measurement to determine a displacement value;

multiplying the displacement value by an advancement percentage to determine a recommended protrusion setting; and setting an adjustment mechanism on the oral appliance to fix a position of the upper tray relative to the lower tray at the recommended protrusion setting to maintain a position of the patient's upper and lower jaws at a fixed relative position while the patient is wearing the oral appliance.

21. The method of claim 20, wherein the advancement percentage is 70%.

22. The method of claim 20, further comprising, until an optimal protrusion setting is achieved, repeating the following:

setting the adjustment mechanism on the oral application to increase a protrusion setting incrementally;

analyzing changes in daytime sleepiness, snoring levels, or sleep study measures of the patient; and, based on the analysis, determining whether an optimal protrusion setting has been achieved.

23. The method of claim 20, wherein the initial position is a neutral occlusal position of the upper and lower jaws.

24. An oral appliance for treating obstructive sleep apnea or snoring of a patient through maintaining a position of the patient's upper jaw relative to a position of the patient's lower jaw, the appliance comprising:

an upper tray configured to removably affix to a patient's upper teeth;

an upper tongue portion extending outwardly from the upper tray;

a lower tray configured to removably affix to the patient's lower teeth;

a lower tongue portion extending outwardly from the lower tray, wherein the upper tongue portion and the lower tongue portion slidably engage with each other limiting motion of the upper tray relative to the lower tray to a longer common axis of the upper tongue portion and the lower tongue portion, and wherein the upper tongue portion and the lower tongue portion extend outside of the patient's mouth when the upper tray is affixed to the patient's upper teeth and the lower tray is affixed to the patient's lower teeth;

a plurality of locking holes located on one of the upper tongue portion and the lower tongue portion, and at least one locking hole located on the other of the upper tongue portion and the lower tongue portion, wherein the plurality of locking holes correspond to protrusion settings; and an adjustment mechanism having at least one locking post configured to extend through at least one of the plurality of locking holes located on the one of the upper tongue portion and the lower tongue portion and the at least one locking hole on the other one of the upper tongue portion and the lower tongue portion when the two holes are aligned and thereby fix a position of the upper tray relative to the lower tray along the longer common axis, wherein the at least one of the plurality of locking holes located on the one of the upper tongue portion and the lower tongue portion corresponds to a selected protrusion setting.

* * * * *